(12) United States Patent  (10) Patent No.: US 8,032,207 B2
Lapanashvili et al.  (45) Date of Patent: Oct. 4, 2011

(54) COUNTER PULSATION ELECTROTHERAPY APPARATUS FOR TREATING A PERSON OR A MAMMAL

(75) Inventors: Larry Lapanashvili, Winterthur (CH); Christian Stuerzinger, Winterthur (CH); Alexander G. Sulzer, Zurich (CH)

(73) Assignee: CardioLa Ltd., Winterthur (CH)

( * ) Notice: Subject to any disclaimer, the term of this patent is extended or adjusted under 35 U.S.C. 154(b) by 293 days.

(21) Appl. No.: 10/578,585

(22) PCT Filed: Nov. 8, 2004

(86) PCT No.: PCT/EP2004/012618
§ 371 (c)(1),
(2), (4) Date: Mar. 2, 2007

(87) PCT Pub. No.: WO2005/044373
PCT Pub. Date: May 19, 2005

(65) Prior Publication Data
US 2007/0198064 A1  Aug. 23, 2007

Related U.S. Application Data

(60) Continuation-in-part of application No. 10/994,981, filed on Nov. 19, 2004, now abandoned, which is a division of application No. 10/069,333, filed as application No. PCT/EP00/07933 on Aug. 14, 2000, now Pat. No. 6,832,982, which is a continuation-in-part of application No. 09/378,181, filed on Aug. 20, 1999, now Pat. No. 6,450,942.

(30) Foreign Application Priority Data

Nov. 7, 2003 (EP) .................................. 03025661

(51) Int. Cl.
*A61B 5/04* (2006.01)

(52) U.S. Cl. .................. 600/513; 600/509; 600/515
(58) Field of Classification Search .................. 600/513, 600/515, 509
See application file for complete search history.

(56) References Cited

U.S. PATENT DOCUMENTS

| 4,541,417 A | * | 9/1985 | Krikorian ........................ 600/17 |
| 4,753,226 A |  | 6/1988 | Zheng et al. |
| 5,186,171 A | * | 2/1993 | Kuhry .............................. 607/68 |
| 5,836,978 A | * | 11/1998 | Gliner et al. ...................... 607/7 |
| 6,832,982 B1 | * | 12/2004 | Lapanashvili et al. .......... 600/16 |
| 2001/0029338 A1 | * | 10/2001 | Krishnamachari ........... 600/515 |
| 2002/0058972 A1 | * | 5/2002 | Minogue et al. ................ 607/72 |

FOREIGN PATENT DOCUMENTS

| EP | 0847776 A1 |  | 6/1998 |
| EP | 1078649 A1 | * | 2/2001 |
| WO | WO 98/05379 | * | 2/1998 |
| WO | WO 98/05379 A1 |  | 2/1998 |
| WO | WO 01/13990 A1 |  | 3/2001 |

\* cited by examiner

*Primary Examiner* — Niketa Patel
*Assistant Examiner* — Nicole F Lavert
(74) *Attorney, Agent, or Firm* — Kilpatrick Townsend & Stockton LLP

(57) ABSTRACT

An electrotherapy apparatus has a sensor for detecting periodically recurring signal peaks, in particular the R-R peaks of an electrocardiogram of a person and a processor for deriving from the periodically recurring signal peaks a time delay corresponding to approximately the end of the next T wave. A trigger system or circuit is initiated by an output signal of the processor or is embodied within the processor for applying electrical stimulations to one or more active electrodes provided on the person at a time that is related to the end of the time delay. The apparatus has a plurality of output channels for applying electrical stimulation to the one or more active electrodes on the person.

9 Claims, 9 Drawing Sheets

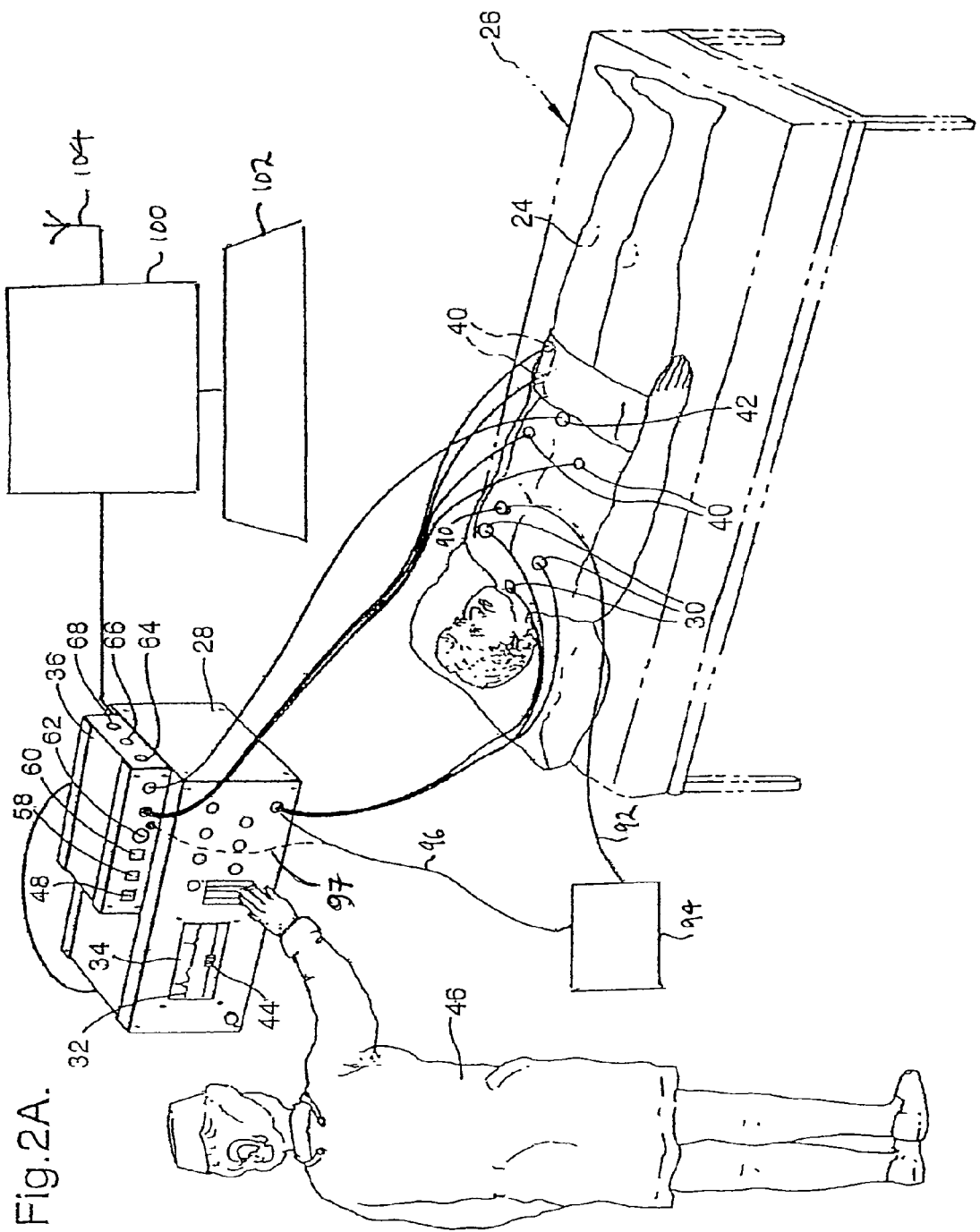

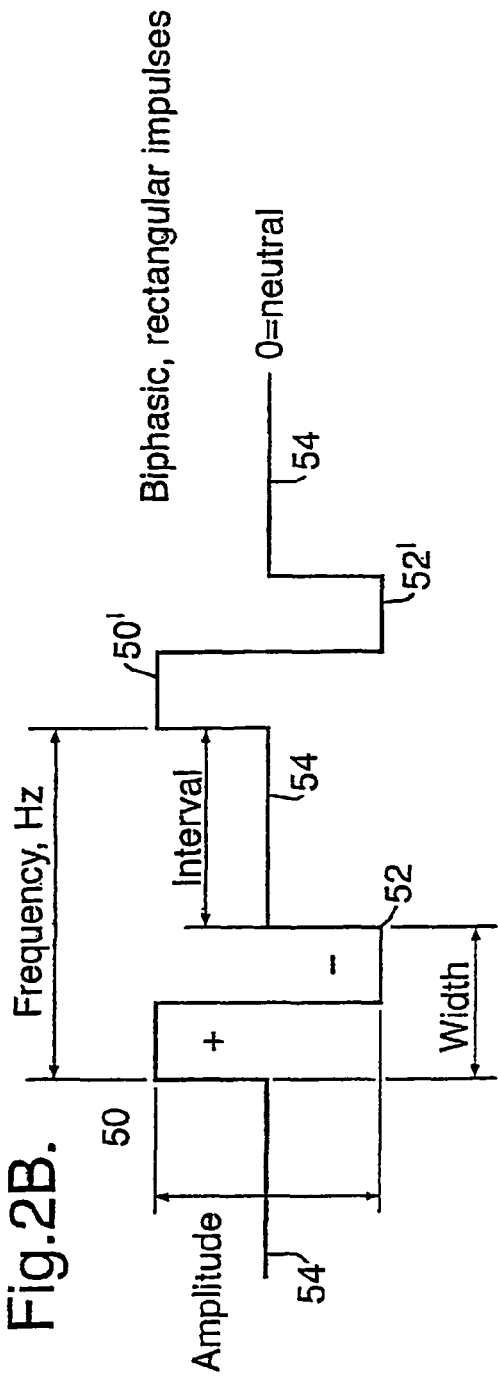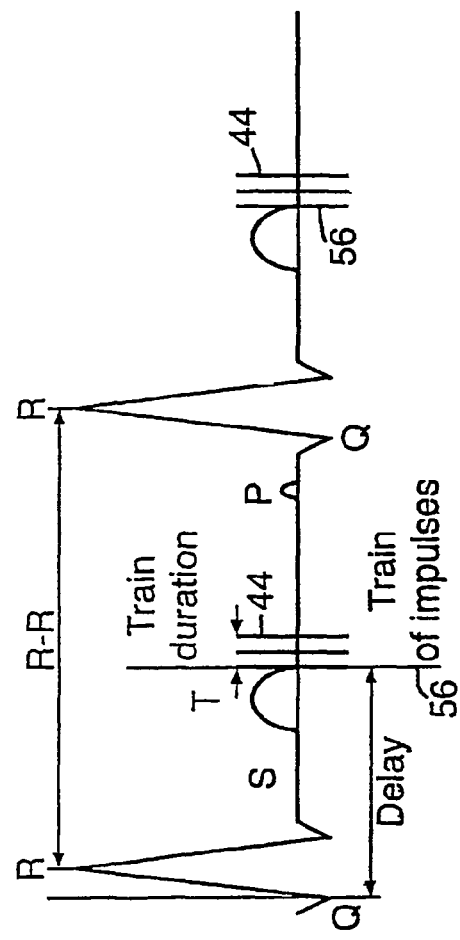
Fig.2B.
Fig.2C.

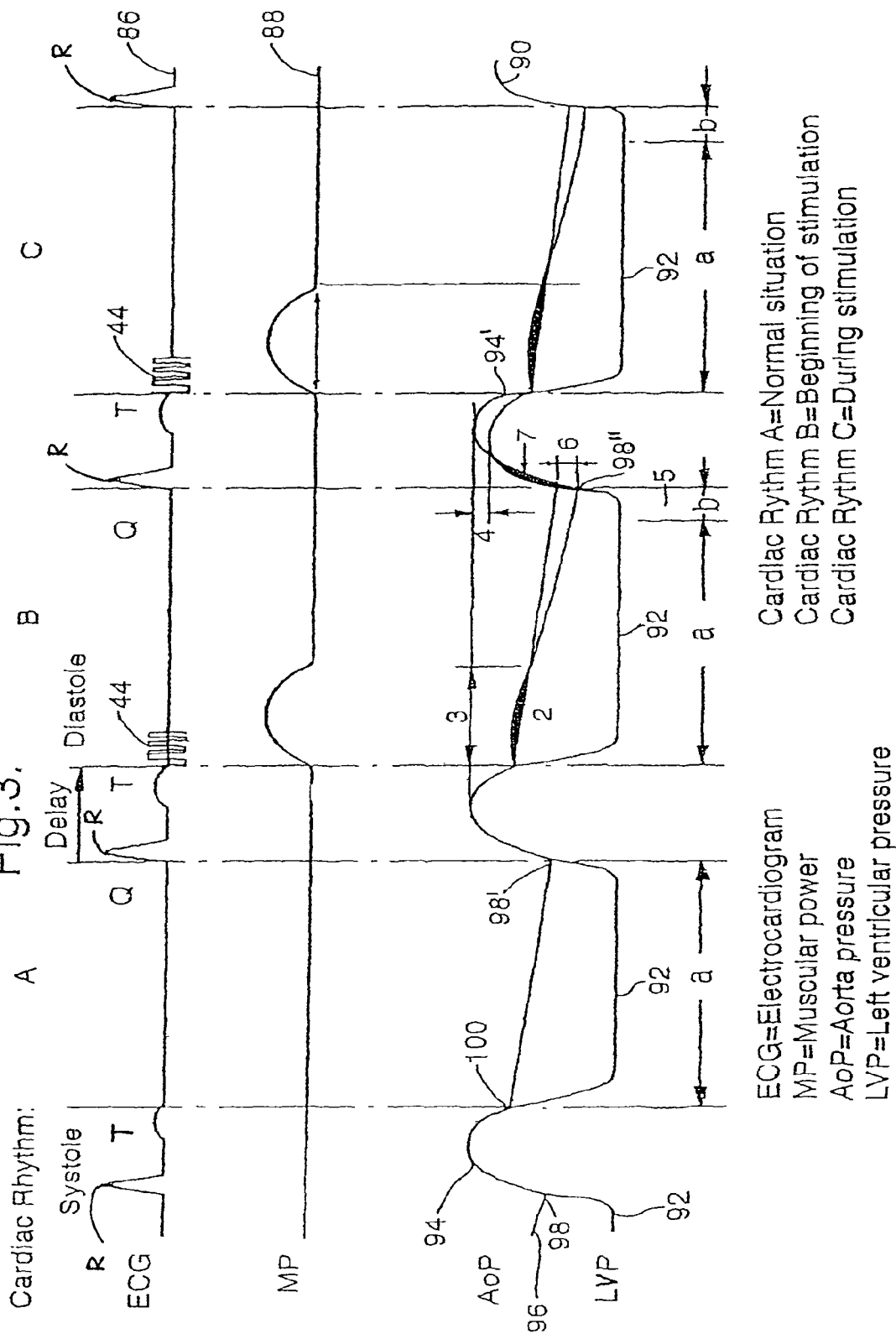

Offset with channel groups A & B on the same electrode

Multiple channel groups with offset

COUNTER PULSATION ELECTROTHERAPY APPARATUS FOR TREATING A PERSON OR A MAMMAL

RELATED APPLICATIONS

This application is a continuation-in-part of application Ser. No. 10/994,981 filed Nov. 19, 2004, which application is a divisional application of application Ser. No. 10/069,333 filed Jul. 15, 2002, now U.S. Pat. No. 6,832,982, filed as a 371 application of International Application No. PCT/EP00/07933, filed on Aug. 14, 2000, which is a continuation-in-part application of application Ser. No. 09/378,181 filed Aug. 20, 1999, now U.S. Pat. No. 6,450,942, the disclosures of which are incorporated herein by reference.

BACKGROUND OF THE INVENTION

The present invention relates to an electrotherapy apparatus comprising a sensor for detecting periodically recurring signal peaks, in particular the R-R peaks of an electrocardiogram of a person, a processor for deriving from the periodically recurring signal peaks a time delay corresponding to approximately the end of the T-wave, and a trigger system or circuit initiated by an output signal of the processor or embodied within the processor for applying electrical stimulations to one or more active electrodes provided on the person at a time related to the end of the time delay. Furthermore the invention relates to methods of using such electrotherapy apparatus.

Electrotherapy apparatus of the initially named kind is described in the international patent application with the publication number WO 01/13990 A1, now expired.

The electrotherapy apparatus described there is adapted to stimulate the muscles of the body of a person or a mammal using so-called counter-pulsation. That is to say, the momentary heart beat of the person or mammal is determined generally by detecting the R peaks of an electrocardiogram derived in real time from the person or mammal being treated. From the distance in time measured between the last two R peaks a time is calculated corresponding to the end of the T-wave of the electrocardiogram using the known so-called Bazett relationship. The electro-stimulation pulses are then applied to the selected muscle generally starting within a window which extends from 5% of the length of the R-R path before the end of the T-wave to a position up to 45% of the length of the R-R path after the end of the T-wave.

It has been found that this type of electrotherapy leads to extremely beneficial effects with respect to the heart of the person or mammal and, depending on precisely how the electrotherapy is carried out, can also be used for curing a whole spectrum of adverse conditions.

In the aforementioned document WO 01/13990 the beneficial effect is primarily attributed to the specific shape of the curve in FIG. 3 of that reference showing a hump in the blood pressure curve just after the onset of diastole which considerably increases the flow through the coronary arteries of the patient concerned, thus leading to an improvement of the condition of the heart muscles.

The experiments conducted to date seem to suggest that this explanation is only part of the story and that in fact even quite small local stimulations of a person or patient can lead to increased perfusion in the small peripheral blood vessels resulting in a significantly lower back pressure on the heart which itself improves the working of the heart. It is believed that some form of bio-feedback is taking place via the autonomous nervous system and that this accounts for the astonishing results that have been achieved.

The aforementioned document WO 01/13990 describes that, although the treatment can be carried out using just one neutral electrode and one active electrode, it is better if a plurality of active electrodes are used. The reason is that the human body becomes accustomed to the applied pulses and, if only one active electrode is provided, then the muscles affected by the electro-stimulation signals gradually become tired and are stimulated less effectively. By applying the stimulating pulses to different active electrodes in sequence it is possible to ensure that the muscle groups affected by the applied impulses do not become tired. It is stated that the minimum number of active electrodes for sequencing is two and a specific embodiment is described in which the train of stimulating pulses is applied in sequence to first, second, third and fourth electrodes.

The apparatus described in WO 01/13990 is provided with a safety cut-out function, meaning that the apparatus switches off automatically if the patient's heart rate goes too high or too low, or if a patient's blood pressure becomes too high or too low or when arrhythmia is detected.

The prior art reference also describes a problem called interference.

This problem can be described as follows. When using any measured heart QRS trace (an electrocardiogram), a trigger signal for detecting the patient's heart rate is usually derived from the positive rising slope of every R peak. The trigger signal is generally a digital trigger signal and initiates the electrical muscle simulation signal after the required delay at a time within the time delay window described earlier. Since this stimulation signal is an electrical signal with a magnitude many times higher than the heart rate signal itself, the electrical stimulation impulse is transmitted on the human body and consequently the heart signal sensor also senses the electrical stimulation signal. If now the control setting of the electrotherapy apparatus is such that a stimulation pulse for the muscle is delivered in counter-pulsation to the heart (i.e. at the end of the T-wave), the trigger unit first receives from the heart rate sensor the wanted trigger input representing an R peak. Moreover, during the R-R cycle, exactly at the moment of the muscle stimulation, a much higher electrical stimulation signal is delivered to the muscle which is interpreted as another R peak and results in a further trigger signal. This trigger signal then leads to a second unwanted muscle stimulation within the same R-R cycle at exactly the same delay but now after the further trigger signal. This second unwanted stimulation is perceived by the stimulated person as a sudden surprising disturbance which is completely irregular in comparison to the calming rhythm expected from the counter-pulsation mode. As a result the heart rate immediately increases sharply, probably via neuro-transmission to the brain and back to the heart. Synchronized stimulation counter-pulsation does not work when such interference is present and the wanted heart load reduction cannot then be achieved.

In order to overcome this problem the reference WO 01/13990 provides a gating mechanism which effectively closes an interference window after a trigger signal from a heart rate sensor has been registered by the electrotherapy apparatus. This interference window is reopened by the electrotherapy apparatus in time to accept the wanted trigger pulses but to avoid unwanted trigger pulses resulting from electro-stimulation.

The WO reference describes one practical execution of the gating mechanism defining the interference window. This gating mechanism is realized in the form of software controlling a microprocessor whereby the rising edge of the digital trigger signal triggers the microprocessor into an interrupt routine and then the closing of the interference window is activated by a software gate which disables the acceptance of any unwanted trigger signal. Thus a further trigger signal resulting from electro-stimulation is prevented from being transmitted to the microprocessor as long as the interference window is closed. Closing and opening of the interference window is set by programmable adjustable setting values which are selected relative to the measured R-R cycle.

The WO reference also describes a practical programmable algorithm which defines the way an adaptive control unit in the electrotherapy apparatus can automatically find the lowest possible heart load. In accordance with the description given in the WO reference, first of all realistic minimum and maximum values for the delay are defined, i.e. for the delay from each R peak to the triggering of a stimulation signal. These limits are set relative to the prevailing heart rate as measured from successive R-R peaks. The minimum delay will usually be selected at or just before the start of the delay window, i.e. at or just before a time corresponding to 5% of the R-R path before the expected end of the T-wave, for example as calculated using the so-called Bazett relationship. As a safety precaution a maximum delay can also be selected which should not be later than 45% of the length of the R-R path after the end of the T-wave. The maximum delay could, however, be omitted.

An offset value is now defined and is added to the minimum delay and used to define the time at which stimulation signals start. A typical initial value for the offset could be 5% to 10% of the R-R paths. Stimulation is now commenced using this time delay; i.e. minimum delay plus offset and the heart rate are monitored by measuring the distance between successive R-R peaks. If a reduction of the heart rate, i.e. a lengthening of the R-R path, occurs, then a reduction in the offset is effected by a predetermined amount, for example a fixed fraction of the original offset, and a check is again made as to whether the heart rate has reduced. If so the offset is again reduced and this process is continued until no further reduction in the heart rate is detected, or alternatively, until the minimum heart rate set in the safety cut-out has been reached or until the heart rate increases again.

A renewed increase in the heart rate indicates that the delay (minimum delay plus offset) is no longer at an optimum value.

If the heart rate increases then the offset should also be increased in an attempt to reduce the heart rate. Once the heart rate starts to increase again then this is an indication that the offset is now too large. This signifies that the optimum value of the offset has been found, namely the value of the offset which resulted in a minimum heart rate. The offset can now be returned to this optimum value. Once a suitable offset value has been determined it can be retained for future use.

Although the WO reference provides a practical system for determining the required offset or the total time delay from each R peak to the triggering of a stimulating electrical pulse, and also practical realizations of the electrotherapy apparatus, there is scope for improvement, particularly with patients suffering from arrhythmia. In patients with such arrhythmia, an irregular heart beat, this means that reliance on a previously measured distance between two R-R pulses in order to determine the time at which a stimulating electrical signal should next be triggered can lead to triggering at undesired times and to discomfort for the patient.

Moreover, although the existing apparatus as described in the WO reference can be used in many applications with beneficial effect there is a desire to increase the performance of the electrotherapy apparatus and to increase its scope of use.

SUMMARY OF THE INVENTION

Accordingly, the present invention is based on an object of firstly providing an improved electrotherapy apparatus having an improved scheme for determining the time at which electro-stimulation pulses are to be transmitted, particularly when a patient is suffering from arrhythmia, and also on the object of providing improved electrotherapy apparatus which can be used for a wider spectrum of treatments, including novel treatments.

In order to satisfy this object there is provided, in accordance with a first aspect of the present invention, an electrotherapy apparatus of the initially named kind which is characterized in that the processor is adapted a) to make a determination for successive pairs of signal peaks of a value corresponding to the time between the successive pairs of signal peaks and thus to the person's heart rate,
b) to compare the value with maximum and minimum permissible technical limits permitted by the apparatus and/or
c) to compare the value with maximum and minimum permissible selected limits,
d) to determine whether each value exceeds a preceding value, or a preceding value averaged over a plurality of heart beats, by more than a defined amount,
e) to determine whether each value is less than a preceding value, or a preceding value averaged over a plurality of heart beats, by more than a defined amount, and
f) to trigger the trigger system only when the comparisons b) and/or c) are favorable and the determinations d) and e) show that the value does not exceed the preceding value, or the preceding average value, by more than the defined amount and is not less than the preceding value, or the preceding average value, by more than the defined amount.

Thus, in accordance with feature a) the electrotherapy apparatus of the present invention first makes a determination for successive pairs of signal peaks, for example R-R peaks, of a value corresponding to the time between the successive pairs of signal peaks and thus to the person's heart rate. The electrotherapy apparatus will have certain inbuilt maximum and minimum permissible technical limits for the heart rate of a person to be treated, for example a minimum limit of 30 beats per minute and maximum limit of 250 beats per minute. If the detected heart rate lies outside of these limits, possibly due to arrhythmia, then it is clear that the apparatus cannot cope with such an unusual heart rate and no electrical stimulation will be generated.

Furthermore, it will generally be preferable to set maximum and minimum permissible selected limits which are tighter than the technical limits referred to above. For example, for a particular patient, the treating physician could select a lower limit of 40 beats per minute and an upper limit of 170 beats per minute, thus making a conscious decision not to treat a patient when the heart rate falls outside of these limits. Thus the processor of the electrotherapy apparatus will also compare whether the value determined for the heart rate lies within or outside of the maximum and minimum permissible selected limits. If the selected limits are used, then these must in any event lie within the maximum and minimum permissible technical limits and it will be sufficient to carry out only the comparison of step c). On the other hand, if no maximum and minimum permissible selected limits are used then it would also be sufficient to carry out only the comparison in accordance with step b).

A determination is now made by the processor (typically a microprocessor or microcontroller) as to whether the value determined for the last R-R path exceeds a preceding value for the R-R path, generally the immediately preceding value (but possibly also a representative value, e.g. from an earlier heart cycle or earlier measurement), or a preceding value averaged over a plurality of heart beats, by more than a defined amount. In addition a determination is made as to whether each determined value for the length of the last R-R path is less than the preceding value, or a preceding value averaged over a plurality of heart beats, by more than a defined amount. If the current value exceeds a preceding value, or a preceding value averaged over a plurality of heart beats, by more than the defined amount, or is less than a preceding value, or a preceding value averaged over a plurality of heart beats, by more than a defined amount, then it is assumed that the patient's heart beat is irregular due to arrhythmia and no electro-stimulation is triggered. If however the value lies within the set limits, then a gating window is first shut to preclude the sensor detecting a spurious peak caused by subsequent electro-stimulation, or at least to exclude any spurious peak detected by the sensor. The electro-stimulation signal is then triggered and electro-stimulation is carried out. At a time before the next expected R peak the interference window is then opened again so that the sensor can detect a next R peak, and the calculation and comparison process described above can be repeated.

Should the next R peak not be detected within an expected time then this can indicate that it arrived earlier, i.e. before opening of the interference window. Alternatively it will arrive significantly later than the expected time and this indicates that the patient's heart beat is irregular, i.e. arrhythmia is present, and the electrotherapy apparatus will wait until further R peaks have been detected which are within the limits described above and electro-stimulation will then begin anew.

Although it is basically considered perfectly adequate to base the operation described above on the last measured R-R path length it is more reliable still if the procedure described above is not carried out simply based on the last measured elapsed time between two successive R peaks but rather on a preceding average value of R-R.

Particularly beneficial when using an average value formed from a plurality of past R-R values is a system in which the plurality of past values considered only includes those values which lie within a range between the preceding measured value plus a predefined positive deviation, such as the defined amount, and the previously measured value less a predefined deviation, such as the defined amount.

In order to increase not only the reliability of the apparatus when arrhythmia is present but also to expand the scope of the apparatus there is provided an electrotherapy apparatus comprising a sensor for detecting periodically recurring signal peaks, for example the R-R peaks of an electrocardiogram of a person, a processor for deriving from the periodically recurring signal peaks a time delay corresponding to approximately the predicted end of the T-wave, and a trigger system initiated by an output signal of the processor or embodied within the processor for applying electrical stimulations to one or more active electrodes provided on the person at a time related to the end of the time delay, characterized in that the apparatus has a plurality of output channels for applying electrical stimulations to the one or more active electrodes provided on the person. For each channel a respective offset value is added to the delay.

Thus if all the channels are connected to an active electrode overlying one muscle or muscle group then they can apply stimulating pulses to the electrode at different times. Accordingly, as the muscle contraction triggered by the first stimulating pulse from the first channel starts to abate, a renewed electrical stimulation signal is applied to it by the second channel at a time later than the first electrical stimulation signal from the first channel and the contraction of the muscle is again enhanced. In this way the total duration of the muscle contraction can be extended. In a similar way the electrical stimulation signal from the third channel can be provided with a different offset, greater than the offset of the electrical stimulation signal provided by the second channel, and again maintains the contraction of the muscle for a longer period. The same situation can be repeated using the fourth channel. In this way it is possible to ensure that the muscle contraction lasts for the maximum desired time, essentially from the end of the T-wave until a value which lies between 85% and 95% of the total R-R path as measured from the start of the rising flank of the last R peak.

At the time the muscle contraction has actually stopped it is not generally possible to detect the next R peak because it has not yet happened. In view of this the apparatus works on the basis that if one heart beat is measured the next heart beat will have a similar length and the length of the preceding distance between the last two preceding R-R peaks is typically used to determine the timing values for the transmission of the stimulation signals in the four channels.

This technique as described above also makes it possible to use different electro-stimulation signals, i.e. different stimulation signal shapes and values in each channel, which can also be beneficial under some circumstances.

As a further example, if two active electrodes are provided, then the stimulation signals from channels 1 and 3 can each be applied to a respective electrode with the same delay value and then the signals from channels 2 and 4 can be applied to the other respective one of the two electrodes, with the signals in channels 2 and 4 having the same offset values.

An electrotherapy apparatus is particularly preferred in which a plurality of channel groups is provided, with each channel group comprising a plurality of channels. Each channel group preferably has the same number of channels. For example two or three channel groups can be provided and each channel group can comprise four channels.

There are a variety of special ways in which such an apparatus can be operated.

It is for example possible to provide each channel and each channel group with the same time delay. If we assume that four active electrodes are provided for each channel group then each channel of each group can be connected to a respective one of the four electrodes associated with that group. The apparatus can then be operated in such a way that channel 1 first stimulates a muscle or muscle group associated with the first electrode, and channel 2 then applies a stimulation signal to the second electrode, the second electrode being associated with a different muscle or a group of muscles from the first electrode. Channel 3 then applies a third stimulation signal to the third electrode and this stimulates a yet further different muscle or muscle group, then channel 4 applies a stimulation signal to the fourth electrode and stimulates another muscle or muscle group associated with that electrode. This has the benefit that each muscle is stimulated only once every four heart beats and therefore each muscle or muscle group has a relaxation period of three heart beats before it is stimulated again.

If there are a plurality of channel groups then each channel group can be used to stimulate different muscle groups on the body and the total stimulation can be enhanced in this way.

Another way of operating the apparatus is to provide each channel group with a respective time delay generally different from the time delay associated with any other channel group. This can be done by programming the processor to provide a time delay for one group of the channels and to add a respective offset time to the time delay for each further channel group.

When using an apparatus configured in this way each channel group of output channels is associated with a group of muscles in general proximity to one another on a body of a person or mammal, with the group of muscles associated with each group of output channels being the same group of muscles for each group of output channels, then the stimulation signals transmitted by each group of output channels can be offset time-wise in relation to stimulation signals transmitted by any other group of output channels. Thus, for example if each group comprises four output channels and four electrodes are provided, a first stimulation signal can be applied to electrode 1 via channel 1 of group 1, a second stimulation signal can be applied during the next heart beat to the second electrode, a third stimulation signal can be applied to a third electrode during a third heart beat and a fourth stimulation signal can be applied to the fourth electrode during a fourth heart beat. The additional offset for the channels of the second group then makes it possible to apply during the first heart beat a second stimulation signal to the first electrode, for example from channel 5 of the second group, to apply a second stimulation signal to the second electrode from channel 6 of the second group and so on. Thus again each muscle is only stimulated in total once per heart beat but is supplied with a plurality of stimulating impulses to prolong the muscle contraction.

Another way of using an apparatus design in this way is for each channel group of output channels to be associated with a group of muscles in general proximity to one another on a body of a person or mammal, for the group of muscles associated with one group of output channels to differ from a group of muscles associated with any other group of output channels and for the stimulation signals transmitted from each group of output channels to the respectively associated group of muscles being triggered at the same time for each group of channels.

Thus all muscles are stimulated in phase, from the associated group of channels, and again by using four channels for each muscle or group of muscles a rest period of effectively three heart beats can be provided for each group of muscles.

In another way of using an apparatus of the above-described kind, when each channel group of output channels is associated with a respective muscle or group of muscles in general proximity to one another in a body of a person or mammal, the group of muscles associated with one group of output channels differs from the group of muscles associated with any other group of output channels and the stimulation signals transmitted from each group of output channels to the respectively associated group of muscles are triggered at different times for each group of channels.

More specifically, the group of muscles respectively associated with each group of channels can be disposed on a body of the person or mammal such that a group of muscles closer to the heart and associated with one group of channels is stimulated later than a group of muscles disposed further from the heart and associated with another group of channels. This has the effect that blood can be pumped by the muscle contraction from the periphery towards the heart.

Alternatively, the group of muscles respectively associated with each group of the channels can be disposed on a body of a person or mammal such that a group of muscles further from the heart and associated with one group of the channels is stimulated later than a group of muscles disposed closer to the heart and associated with another group of channels. This helps to pump blood from the heart to the periphery of the body and can be of benefit in increasing the blood flow through a particular part of the body, for improving the blood flow to that part of the body, for example for recovery after an injury, and can also be used to benefit lymph transport in the body.

The invention will now be described in more detail by way of example only with reference to the accompanying drawings in which FIGS. 1 to 4 are generally similar to FIGS. 1 to 4 of the above-mentioned document WO 01/13990, but with certain modifications in FIGS. 2a and 4, and in which the remaining Figures pertain specifically to embodiments of the present invention.

BRIEF DESCRIPTION OF THE DRAWINGS

FIG. 2A is a schematic diagram of a first variant of an apparatus for applying electro-stimulation in accordance with the present invention, FIG. 2B is a graph illustrating the terminology used to describe a biphasic rectangular impulse, FIG. 2C is a graph illustrating the timing of the pulses applied to a patient in the counter-pulsation mode to achieve cardioresonance in accordance with the invention, FIG. 3 is a set of diagrams showing the effect of the method and apparatus of the invention on the operation of the heart of a patient.

DESCRIPTION OF THE PREFERRED EMBODIMENTS

Figure 1A:
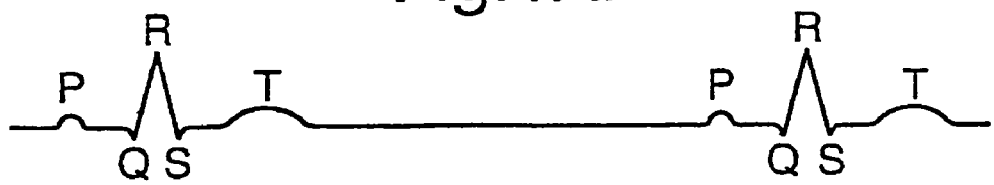
FIG. 1A is a schematic diagram illustrating a typical electrocardiogram.
Figure 1B:
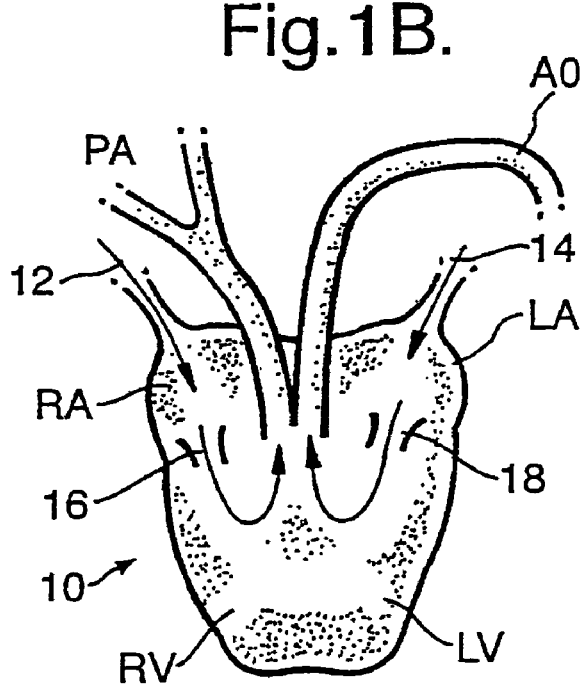
FIG. 1B is a schematic diagram of the human heart.
Figure 1C:
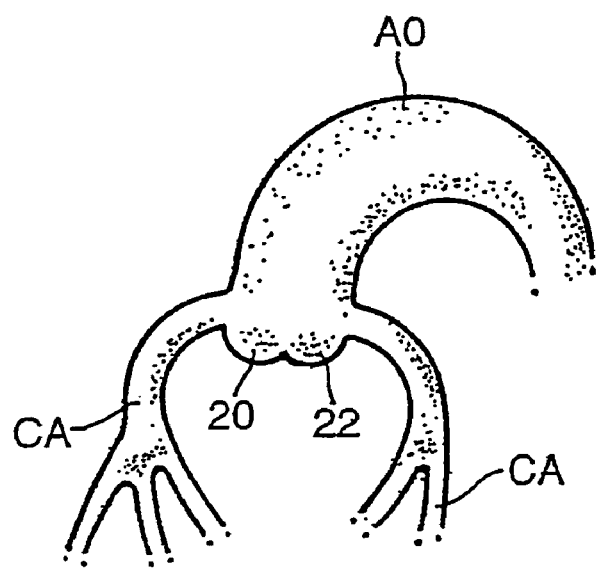
FIG. 1C is an enlarged view of the aorta at the junction with the heart and with the coronary arteries.

Turning now to FIGS. 1A, 1B and 1C, a brief description of the normal operation of the human heart will be given in order to facilitate an understanding of the present invention.

The heart 10 shown in FIG. 1B has four chambers, namely the right atrium RA, the right ventricle RV, the left ventricle LV, and the left atrium LA. Venous blood returning to the heart flows into the right atrium, then into the right ventricle and passes to the lungs via the pulmonary artery PA. In the lungs the blood picks up oxygen and returns to the left atrium LA, as indicated by the arrow 14. From there, the oxygenated blood passes into the left ventricle, and then into the aorta AO where it starts on its journey through the so-called big circulation around the body. The circulation from the right ventricle to the lungs and then to the left atrium is called the minor circulation.

The operation of the heart is associated with electrical signals, which are shown on the electrocardiogram of FIG.

1A. The point P signifies the contraction of the two atriums RA and LA, which pushes blood into the respective ventricles RV and LV via the respective valves 16 and 18, which act as non-return valves. The section of the electrocardiogram starting with Q and ending with T is referred to as the systole and represents the ventricle contraction which serves to expel blood from the right ventricle into the pulmonary artery, and from the left ventricle into the aorta. During this contraction, the valves 16 and 18 are closed to prevent reverse flow into the right atrium and the left atrium. The section TQ is referred to as the diastole, meaning the relaxation or expansion of the ventricles. The heart is supplied with oxygenated blood via the coronary arteries CA, which branch off from the aorta just upstream of the valves 20, 22, which close to prevent blood returning from the aorta to the left ventricle during the diastolic phase. Clearly the heart, itself a muscle, must be supplied with oxygenated blood to keep the muscles working. The heart is supplied with this oxygenated blood via the coronary arteries CA during diastole. At T the valves 20, 22 of the aorta AO are closed and at this time the blood pressure in the aorta causes blood to enter the coronary arteries CA. Accordingly, an increase of the pressure in the aorta AO during diastole favors the coronary arteries.

As will be seen from the following, one of the important results associated with the present invention is a small increase in pressure in the aorta during diastole and this has been found to have a profound effect on the operation of the heart muscle.

FIG. 2A shows an illustration of a basic apparatus which has been used for the testing of the present invention and which clearly also represents a perfectly viable apparatus for practicing the invention, although a whole variety of further improvements and developments are possible, as will be described later.

As shown in FIG. 2A, a patient 24 is shown lying on a bed 26 and is connected to an electrocardioscope 28 via (in this embodiment) three sensing electrodes 30, which enable the electrocardioscope to show the ECG trace 32 for the particular patient 24 on the display 34. From the information available to the electrocardioscope through the three electrodes 30, a signal is extracted corresponding to the repetition frequency of the path R-R of the ECG trace of FIG. 1A. That is to say, this signal represents the frequency at which the patient's heart beats, i.e. his pulse rate.

Figure 4:
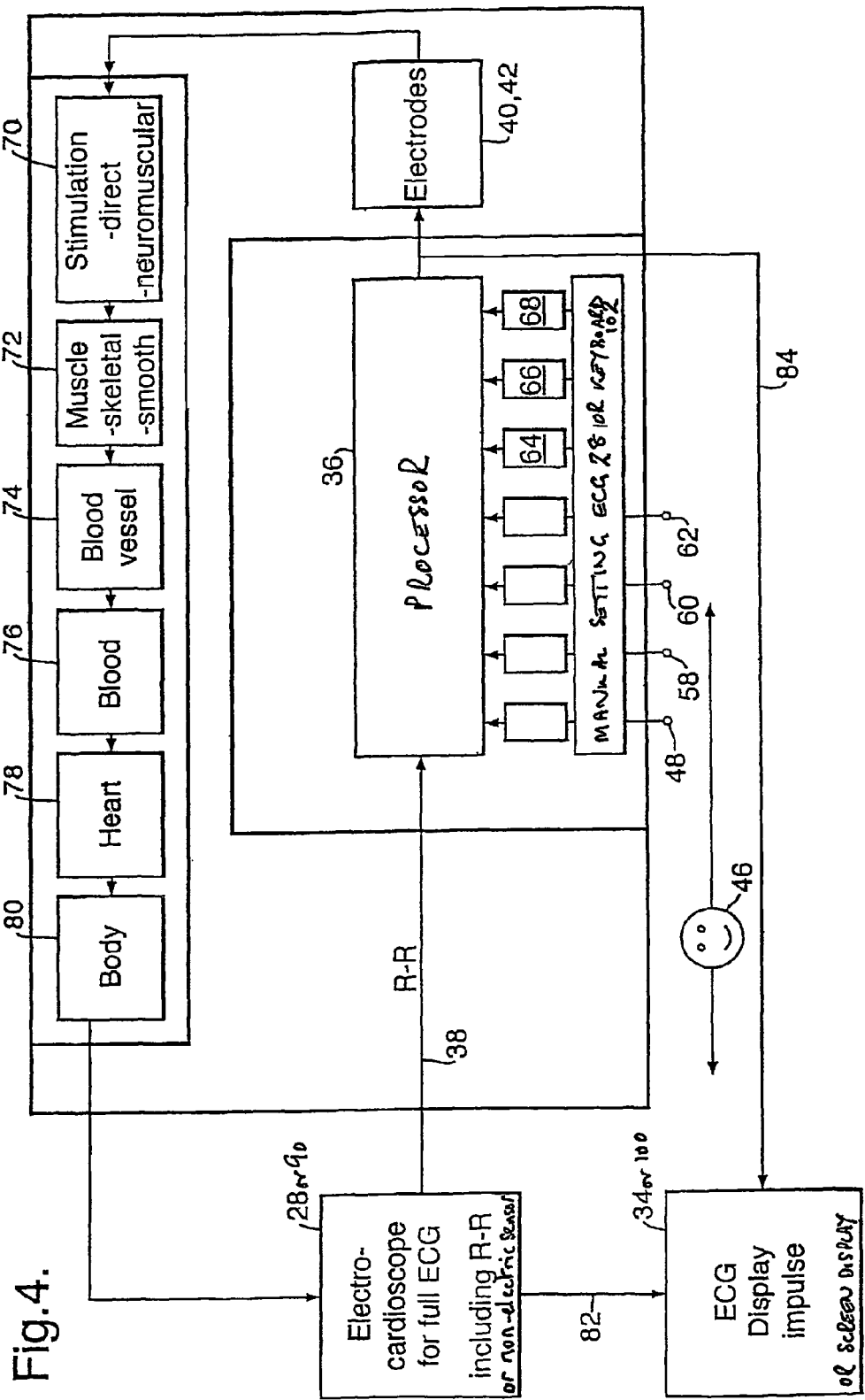
FIG. 4 is a schematic diagram illustrating the operation of an apparatus similar to that of FIG. 2A.

This signal is fed via a line 38, which is not shown in FIG. 2A but which is schematically illustrated in the diagram of FIG. 4 relating to the operation of the apparatus of FIG. 2A, to a processor 36 with an associated trigger system. In this embodiment the trigger system is embodied in the processor and suitable software is provided so that the trigger system delivers a train of biphasic rectangular pulses to the patient 24 via the active electrodes 40, of which four are shown in FIG. 2A. The precise shape of the train of biphasic rectangular pulses will be described later with reference to FIG. 2B. Although the trigger system is embodied in the processor in this example it could also be a separate unit (not shown) and simply receive trigger signals from the processor. In that case the output channels described here will not generally be present at the processor but at the output side of the separate unit.

The further electrode 42 is a neutral electrode necessary to complete the circuit. As illustrated in FIG. 2C the train of pulses 44 is triggered once per cycle of a patient's heart and is timed to coincide with the end of the T-wave of the electrocardiogram. The train of pulses 44 is also shown on the display 34 of the electrocardioscope, which enables the operator 46 to see the phase relationship between the train of pulses 44 and the electrocardiogram 32.

From the joint display of the ECG and the train of pulses 44 on the screen 34 of the electrocardioscope, the operator 46 can see whether the train of pulses has the appropriate delay relative to the Q-wave to secure the cardioresonance desired in accordance with the invention.

As noted earlier, the train of pulses is preferably set to start at the end of the T-wave. The operator 46 is able to adjust the phase for the start of each train of pulses, i.e. the delay, so that it coincides with the end of the T-wave. This is one manual input into the processor indicated at 48 in FIGS. 2A and 4.

Before discussing the effect the train of pulses 44 applied to the patient has, it is appropriate to discuss the terminology used in this specification with respect to the pulses generated by the input system comprising the pulse generator 36 and the electrodes 40, 42.

The basic output of the pulse generator 36 is shown in FIG. 2B. It can be seen that the train of pulses comprises a plurality of so-called biphasic, rectangular impulses. Each biphasic rectangular impulse has a rectangular positive half pulse 50, and a rectangular negative half pulse 52 immediately following the positive half pulse, so that the impulse width is determined by the width of 50 plus the width of 52. The biphasic impulse 50, 52 of FIG. 2B is then followed by an interval and thereafter by a second biphasic impulse indicated as 50', 52' in FIG. 2B. The distance between sequential positive half waves 50, 50' of the biphasic pulses determines the pulse repetition frequency of the signal. During the interval between sequential biphasic pulses and during the intervals between sequential trains of biphasic pulses, the voltage applied to the electrodes 40 is zero, i.e. is the same as the voltage at the neutral electrode 42, so that no stimulation of the patient occurs. This zero voltage is indicated by 54 in the diagram of FIG. 2B. It will be noted that instead of applying voltages to the electrodes, currents can be applied to them in which case the references above to voltages should be regarded as references to currents.

As noted above, each train of biphasic rectangular pulses is timed to start at the end of the T-phase of the ECG, i.e. at points 56 in the diagram of FIG. 2C, which shows an enlarged section of an ECG trace with the impulse trains 44 superimposed on it. In one specific example, the pulse repetition frequency of the biphasic rectangular pulses of each train is typically selected so that five such pulses occur within the train duration. The train duration is usually selected to correspond to a time equivalent of from 3 to 5% of the R-R path of a human being undergoing treatment.

A typical value of the train duration will amount to 3% of the total duration of the heart beat, i.e. the R-R distance. Thus, the pulse repetition frequency delivered by the pulse generator 36 would, in this example, be five pulses in 0.033% of the duration of a heart beat, which might typically be equivalent to one second, thus resulting in a pulse repetition frequency of the individual pulses of the trains of 150 Hz.

For the purpose of giving a reasonable example, the amplitude of the output signal of the pulse generator 36, i.e. as applied to the electrodes 40, can vary from a positive amplitude 50 of plus 40 V to a negative amplitude 52 of minus 40 V.

It must be stressed that these values are simply given by way of example and that substantial variations may be made, depending on a whole variety of factors.

So far as the amplitude of the biphasic signal is concerned, it has been found that different patients have different threshold voltages at which they perceive the treatment as being uncomfortable. Thus, one possibility is for the operator 46 to vary the amplitude of the biphasic pulses until the patient perceives them as being slightly uncomfortable and then to reduce the amplitude slightly so that the patient suffers no discomfort.

Generally speaking, an amplitude with a lower limit starting from slightly above zero volts (say two or three volts) is possible. The upper limit depends on whether the patient feels comfortable with the voltage level applied and the resulting current (very high voltages could be used in theory at least, providing the current is restricted to non-damaging values).

The relationship between the pulse width and the pulse interval of each train of pulses determines the total energy input into the muscles stimulated via the electrodes 40, 42. While a ratio of about 1:5 has been found effective, this ratio can be varied substantially and indeed an interval is not absolutely essential. Generally speaking, with all patients a threshold is reached, depending on the pulse amplitude and the ratio of the pulse width to the interval, at which involuntary contractions of the muscle are apparent to a trained observer and the apparatus will usually be operated with amplitudes and ratios of the pulse width to pulse interval at levels at which apparent involuntary muscular contractions do occur, i.e. above the threshold value.

A particularly important reason for using biphasic pulses is to avoid the onset of electrolysis in the tissue affected by the applied impulses. Any effects of this kind which may be triggered during one half pulse are immediately reversed in the next half pulse. Although biphasic rectangular pulses of the kind described above have been found to be satisfactory and currently represent the preferred type of pulses, they are by no means the only possibility. Generally speaking, it is anticipated that the pulses delivered by the pulse generator will be biphasic in the sense that they have some positive going signal component and some negative going signal component. However, it is not out of the question that single phase rectangular pulses can also be used to advantage in some circumstances. It is certainly not essential that the negative half wave is of the same size and shape as the positive half wave. The positive half wave could be of different amplitude and width from the amplitude and width of the negative half wave. Moreover, it is not essential for the pulses to be rectangular pulses. They could be sinusoidal or they could have some other shape if desired.

As is apparent from FIG. 4, a preferred embodiment of the invention provides the operator 46 with various different parameters which he can set during the treatment of a patient. The first of these is the delay or impulse delay, which, as shown in FIG. 2C, is the time difference between the Q wave end of a QRS heart signal and the effective start of the impulses, i.e. the start of the train or burst of impulses which commences at the end of the T-wave. The operator 46 has the possibility of adjusting this delay at 48, for example, by varying a potentiometer which determines the delay as a percentage of the measured R-R path length, or by keying in a corresponding input to the processor, which is then put into effect by the programming of the processor. This is an extremely important adjustment in the apparatus of FIGS. 2A and 4 for the following reason:

As will be explained shortly, the effect of the pulses is to unload the heart. This manifests itself by a reduction of the pulse rate, i.e. of the frequency of the heart beat. This means that the time between successive R peaks of the ECG trace increases. Not only does R-R increase, but the distance from Q to the end of the T-wave also increases because it stands in a known relationship to the time interval R-R. Thus, if the delay were a fixed value, the start of the train of pulses 44 would not always coincide with the end of the T-wave due to the change in the pulse rate. Accordingly, when the operator sets the delay, this does not mean that he sets a specific value for the delay in milliseconds but rather that he specifies the delay as a specific percentage of the measured R-R path length.

The best results are frequently obtained when the delay is timed so that the first train of pulses is initiated at the end of the T-wave. However, beneficial results can also be obtained if the train of pulses starts later than the end of the T-wave and, indeed, in some applications of the apparatus this is a desirable feature, as will become apparent from the later description.

Practically speaking, it is considered desirable to keep the start of the train of electrical stimulating pulses within a window between 5% of the length of the R-R path before the end of the T-wave of an electrocardiogram and 45% of the length of the R-R path after the end of the T-wave, and the start of the train of electrical stimulating pulses can be selected within this range.

Another parameter which can be varied by the operator 46 is the duration of the train of pulses applied to the patient after the end of each T-wave. As shown in FIG. 2C, the duration of a train is defined as the time between the start and the end of the impulses within a train or burst of impulses. This possibility of variation is indicated in FIG. 4 by the reference numeral 58.

The train itself is the package of electric impulses which are repeated one after the other for the time defined by the duration of the train. The number of electric impulses in each train can be varied by varying the output frequency of the biphasic pulses, i.e. the pulse repetition frequency of the biphasic pulses in each train of pulses, i.e. the number of pulses that are repeated per second if the train of pulses were to be one second long. Furthermore, the duration of the train determines how long the stimulation with a given frequency is repeated, i.e. how many impulses are effectively delivered within one heart cycle. This frequency and the duration of the train can be varied by the operator 46 at the input 60 in the example of FIG. 2A and FIG. 4. The other variable which can be readily changed by the operator 46 in the embodiment of FIGS. 2A and 4 is the amplitude of the biphasic rectangular impulses, i.e. the maximum difference between the peak value of the positive half cycle 50 and the peak value of the negative half cycle 52, as shown in FIG. 2B. This possibility of adjustment is indicated at 62 in FIG. 4. The amplitude is normally measured as a potential difference in volts. In an alternative embodiment (not shown) it is possible to plot a current curve rather than a voltage and to vary the amplitude with reference to the corresponding peak amplitude of the current curve.

In the apparatus of FIGS. 2A and 4 there are three further parameters of the pulses which are fixed, i.e. cannot in this embodiment be varied by the operator 46. The first of these parameters is pulse width, i.e. the time before the start and end of an electric impulse, as shown in FIG. 2B. The pulse width is selected in the example of FIGS. 2A and 4, so that the interval at a pulse repetition frequency of 150 Hz is 5.66 times as long as the pulse width. That is to say, by fixing the pulse width the interval will automatically vary as the pulse repetition frequency is varied. If the pulse width is made variable, as it is in some other embodiments, then varying the pulse width automatically results in the interval shown in FIG. 2B varying, on the assumption that the repetition frequency of the pulses of the train of pulses does not change. Box 64 in FIG. 4 relates to the input at which the fixed value of the pulse width is selected.

The further boxes 66, 68 in FIG. 4 represent two further parameters of the output of the pulse generator, which in the apparatus of FIG. 2A and FIG. 4 are fixed and not readily variable by the operator 46. Box 66 relates to the impulse form, i.e. the geometric form of the electric impulse resulting when the amplitude of the electric impulse is displayed over the entire impulse width. In the present example this is a biphasic rectangular pulse but it could have different shapes, for example sinusoidal or saw-toothed.

Box 68 refers to the possibility of changing the impulse mode which relates to the alternating mode of how impulse forms are repeated between electric positive and electric negative phases of impulses. In the present example the impulse mode is clearly biphasic, with positive and negative, but otherwise identical electric impulses alternating one after the other. This mode switch would, however, allow the operator to select some other mode, for example two positive half pulses followed by one negative half pulse.

One other aspect of the invention should also be mentioned with reference to FIG. 2A. This is the possibility of using a plurality of electrodes 40, 42. As mentioned above, the electrode 42 is a neutral electrode and it is only necessary to provide one such neutral electrode. However, more than one neutral electrode can be used when different areas of the body are treated, in order to allow a neutral electrode to be in the vicinity of each active electrode or each group of active electrodes. For long-term treatment of a patient it is recommended to provide a plurality of active electrodes 40.

The reason is that the human body can become accustomed to the applied pulses and if only one active electrode 40 is provided, i.e. only one electrode to which the biphasic rectangular impulse signal of FIG. 2B is applied, the muscles that are stimulated by the potential between this electrode and the neutral electrode 42 gradually become tired and are stimulated less effectively. By applying the stimulating impulses to the different active electrodes 40 in sequence, it is possible to ensure that the muscles of the muscle group affected by the applied impulses do not become tired. The minimum number of active electrodes for sequencing is two.

Experiments have shown that by applying the output signal of a pulse generator to several electrodes 40 in sequence the treatment can be carried out over a period of many days without problem, and indeed only two electrodes are sufficient for this. However, four electrodes are preferred.

In the experiments done to date the first train of pulses 44 has been applied to the first electrode 40, the next train of pulses has been applied to the second electrode, the next train to the third electrode and the next train to the fourth electrode and the next train to the first electrode and so on. However, a sequence of this kind is not essential. It could be perfectly feasible to feed several trains of pulses to one electrode and then to change to the next electrode, etc. Random energization of the electrodes with successive pulse trains or groups of pulse trains would also be entirely feasible.

It should be emphasized that there is nothing critical in the placement of the individual electrodes 40 and 42. Although these are shown in the stomach region of the patient under treatment here, they could be virtually anywhere on the patient's body. It is a surprising aspect of the present invention that the stimulation of any part of the peripheral vascular system with even small amounts of excitation energy has been found to produce the beneficial effect of the invention.

A more detailed discussion of the types of electro-stimulation possible will be given later in the description.

It will be noted that FIG. 4 also shows with a series of boxes how the stimulation input to the patient from the pulse generator affects the body. Box 70 indicates that the stimulation can be direct stimulation or neuro-muscular stimulation, which is more usual.

Box 72 shows that the stimulation can be applied either to skeletal muscles or to smooth muscles. The effect of applying the stimulation to skeletal or smooth muscles is in both cases to produce a pressure pulsation in a local blood vessel of the peripheral vascular system indicated by the box 74. This local pressure fluctuation propagates via the blood, essentially an incompressible liquid indicated by box 76, to the heart indicated by box 78. Provided the pulses are timed correctly and applied in accordance with the teaching of the present invention, then they have been found to have a significant effect in reducing the heart load, which itself has an effect on the body of the patient indicated by box 80. This effect is picked up by the electrodes 30 of the electrocardioscope.

As noted earlier, a signal corresponding to the pulse rate, for example the R-R signal, is then passed on to the pulse generator and triggers the generation of the biphasic rectangular pulses of the individual pulse trains. The ECG wave form 82 is shown on the display 34 of the electrocardioscope as is the output signal of the pulse generator, as shown by the lines 82 and 84 in FIG. 4. The operator 46 has the ability to vary the impulse delay to ensure that each train of pulses starts at the end of the T-wave of the electrocardiogram or at the position deemed optimal in a particular case.

FIG. 3 gives a graphic representation of the effect of the treatment with the method and apparatus of the invention. The topmost curve 86 shows several peaks of an ECG wave form and is divided basically into three sections A, B and C. Section A shows a patient's cardiac rhythm in a normal situation, i.e. without stimulation. Section B shows the cardiac rhythm for the same patient at the start of stimulation and section C shows the cardiac rhythm during continued stimulation. This division into sections A, B, C also applies to the further curves 88 and 90. In curve 86 section B shows the first train of impulses 44 which starts after the end of the T-wave and lasts for about 15% of the T-Q path. This same wave form repeats in phase C and continues repeating until the stimulation is terminated. The effect of this stimulation is to produce a significant reduction in the patient's heart rate so that the length between successive R positions of the ECG lengthens in the course of time. It will be noted that the R-R pattern in section C is longer than in section A, by a length labeled "b" as shown in curve 90 in FIG. 3.

Curve 88 shows the modulation of the muscular power resulting from the trains of electrical impulses such as 44. In phase A of line 88, there is no stimulation and accordingly the line is a straight line. The first stimulation occurs in the section B and results in a stimulation of a muscle which affects the peripheral vascular system. It will be noted that the muscle contraction 3 starts at the start of the train of pulses 44 and tends to reach its maximum contraction at the end of the train of pulses and then relaxes over a time period slightly longer than the train duration. It will be noted that the train of pulses 44 contains a plurality of stimulating electrical impulses but results in a simple muscular contraction. This muscular contraction 3 produces a pressure pulsation in the patient's peripheral vascular system which propagates back to the patient's heart.

The result of this can be seen from the curve 90, which is in fact a composite curve showing the pressure in the aorta and the left ventricular pressure. The left ventricular pressure starts from a base line value 92 and increases smoothly into a rounded peak 94, which has a value above the base line value 92 from the start of the Q wave until just after the end of the T-wave. Superimposed on this curve is a curve 96 for the pressure in the aorta.

At the point 98 the valves 20, 22 in FIG. 1C open and the pressure in the left ventricle is communicated directly into the aorta so that the pressure in the aorta rises at the same rate and with the same value as the pressure in the left ventricle until the end of the T-wave is reached, i.e. until the point 100 in FIG. 3, where the valves 20, 22 close again and the pressure in the aorta gradually sinks as the blood in it moves through the arteries of the human body. At point 98' the valves 20, 22 open again and the cycle repeats.

The effect of the muscular contraction, indicated by 3 in the curve 90, is to modulate the pressure in the aorta by a pressure wave traveling back to the aorta, from the peripheral blood vessel pulsation induced by the muscle contraction, so that in phase B it is slightly higher—shown as a visible hump—in the region labeled 2 than the corresponding value in phase A of curve 96. However, after the end of the muscular contraction, the pressure in the aorta sinks to lower values than were present in the corresponding section of the pressure curve in phase A.

At the same time it will be noted that the peak 94" of the left ventricular pressure has also reduced relative to the peak value 94 in phase A. The reduction is labeled 4 in FIG. 3.

What this means in practice is that the hump 2 in the pressure in the aorta in diastole results in increased coronary circulation; i.e. more blood and more oxygen are being supplied to the heart muscles, resulting in more energy being made available to the heart. This causes the pulse rate to reduce so that the duration of each heart beat increases from the value a before stimulation by the amount b to the value a+b after prolonged stimulation. The typical measured reduction with various probates is about 10 pulses per minute in the rest mode, for example 70 down to 60, or up to 30 or more at a high pulse rate, for example from 140 to 110, because of an increase of the DPTI/TTI ratio (diastolic blood pressure time index/time tension index).

In addition, the reduction indicated by 4 from the peak value 94 in phase A to the peak value 94" in the phase C represents a fall in the systolic pressure in the left ventricle and thus reducing left ventricular wall tension.

Bearing in mind that the heart load is proportional to the pulse rate times the systolic pressure, the effect of the invention in lowering both pulse rate and systolic pressure leads to a significant reduction in heart load.

The pre-systolic blood pressure, i.e. the pressure at the points 98, 98', 98" in FIG. 3, seems to reduce by about −5 mm Hg for a probate with normal blood pressure of 120/60. Extremely beneficial is the fact that with patients with blood pressure which is too high the reduction is far more pronounced, although the reduction in the heart rate for such patients tends to be less than for normal patients.

It is also noted that the cardioresonance electro-stimulation of the invention not only results in a lower systolic pressure but also a steeper pressure increase in the systole, which can also be seen from curve 90 in phase C of FIG. 3.

Generally speaking, it can be said that DPTI increases by some +10 to 15% depending on probates resulting from the hump in the blood pressure increase in diastole, reduced heart pulse rate and corrected by the difference from reduced pre-systolic blood pressure, assuming probates with normal blood pressure.

TTI decreases by some 4 to 5%, resulting from lower pre-systolic blood pressure corrected by the steeper pressure increase in systole (as shown at 7 in FIG. 3).

The benefit of this is that the DPTI/TTI ratio consequently increases by some 15 to 20% depending on probates for those having normal blood pressure. Thus, the typical heart load reduction is some 10 to 25% or more depending on the probates and their physical conditions, which results from lower heart pulse rate and reduced systolic blood pressure and lower pre-systolic pressure. Furthermore, myocardial contractivity is improved, coronary blood circulation increased and ischemia reduced.

Turning now to FIG. 2a there can be seen a further sensor 90 which is connected by a lead 92 to a sensor signal processor 94 which is in turn connected, for the purpose of illustration, via a lead 96 to the electrocardiograph 28. The sensor 90 is a heart signal sensor of a non-electrical kind. It can for example be an acoustic sensor which detects the heart signal by the different acoustic noises generated during the operation of the heart. The acoustic signals are converted by a transducer into electrical signals and are processed in the device 94 to generate a signal corresponding to the electrocardiogram 32 shown in the electrocardiograph 28.

Various different types of non-electrically operating sensors 90 are known and all can be used for the purposes of the present invention. The benefit of using a non-electrical sensor is that the sensor is not disturbed by the electrical noise resulting from the electrical stimulation of the muscles. In fact, when such a sensor is used, the electrocardiograph 28 is actually redundant and therefore the lead 96 could lead, as is shown in dotted lines by the reference numeral 97, directly to the signal processor 36. Generally speaking, the processor 36, which can be a PC, will be connected to a screen 100 with a keyboard 102 and the operator or physician 46 can then observe the heart trace on the screen (if desired) and can input parameters for the operation of the processor into the computer 100 via the keyboard. In addition reference numeral 104 signifies an internet connection which enables the physician or operator 46 to download new or updated operating programs for its electrotherapy apparatus which are made available as so-called firmware by the manufacturer of the electrotherapy apparatus.

A brief description will now be given as to how the processor 36 basically operates to provide electrical stimulation signals.

The processor either receives signals from the electrocardiograph 28 or from the non-electrical sensor 90 (or from both) and is programmed to recognize the R-R peaks of the electrocardiogram, these being the largest signal peaks and being the easiest to recognize. The processor first makes a determination for each successive pairs of signal peaks of a value corresponding to the time between the successive pairs of signal peaks and thus to the person's heart rate. For example, if the patient has a regular heart beat of 60 beats per minute, then the time between successive pairs of R-R peaks is one second or 1000 milliseconds. Generally speaking, a person's heart rate is not entirely regular and with many patients in need of treatment for heart problems it is definitely irregular. This means that the distance between successive pairs of signal peaks fluctuates and may vary significantly from the 1000 milliseconds of the example given above.

The electrotherapy apparatus of the present invention is designed to deal with heart beats as low as 30 per minute and as high as 250 per minute. Outside of these limits, which are given by way of example only, the electrotherapy apparatus cannot operate and thus, for each successive pair of signal peaks detected, a determination is made of whether the distance between the R-R peaks lies within the range in which the apparatus is physically capable of operating. For example 30 beats per minute corresponds to a time between R-R peaks of 2000 milliseconds, and a heart beat of 250 corresponds to a period of 240 milliseconds. Generally speaking, heart rates of 30 and 250 are extreme and the electrotherapy apparatus preferably has an input, which can be made via the keyboard 102, enabling the operator to set the limits to a narrower range, for example 40 to 170 beats per minute.

The processor 38 is programmed to compare the measured time between each pair of R-R peaks with the range of values technically permitted by the apparatus and/or with the maximum and minimum permissible operator-selected limits. Clearly the operator-selected limits must be narrower then the technical limits, and, if these limits are input by the operator, then it is sufficient simply to make the comparison with these limits. On the other hand, if no limits are selected by the operator, it is only necessary to carry out the comparison with the maximum and minimum permissible technical limits.

The operation of the apparatus basically relies on the heart rate not fluctuating wildly and is specially adapted to cope with the problems that arise if the patient is suffering from irregular heart beat, arrhythmia.

In this connection the processor 36 is first programmed to determine whether the time between successive R-R peaks exceeds a preceding value, i.e. the distance in time between the R-R peaks of the preceding heart beat, or a preceding value averaged over a plurality of heart beats, by more than a defined amount. In addition the processor is programmed to determine whether each measured R-R value is less than a preceding value, again typically the R-R value for the preceding heart beat, or less than a preceding value averaged over a plurality of heart beats, by more than a defined amount.

The processor is programmed, so that it only triggers the generation of an electrical stimulation pulse when the comparison with the maximum and minimum technical limits and/or the maximum and minimum permissible selected limits is favorable and when the determinations referred to above show that the measured R-R value does not exceed the preceding R-R value, or the preceding average R-R value, by more than a defined amount and is not less than the preceding value, or the preceding average value, by more than a defined amount.

If the comparisons are unfavorable or the determinations are unfavorable, then no trigger pulse is generated and the apparatus simply continues measuring the distance between successive pairs of R-R peaks until a plurality of successive values are found which satisfy the above criteria.

In addition the processor is programmed to close a measurement window for the sensor (electrocardiograph or non-electric sensor) once a determination is made that the above comparisons are favorable and the determinations are favorable. When this measurement window is closed no further R-R signals are accepted by the processor until the window is opened again, as will be described in detail further below.

Once the R-R value is known the processor is also able to calculate, using the known Bazett relationship, the number of milliseconds till the expected end of the T-wave for the next heart beat. Rather than calculating this value using the Bazett relationship the processor can also be programmed to look up the corresponding value in a suitable look-up table or other statistical database.

Should the operator or physician decide that the stimulation will not be carried out precisely at the end of the T-wave, but at a slightly earlier or later time, then he can input the required offset value (as a percentage, e.g. by varying the proportionally constant in the Bazett relationship) into the keyboard which will be considered by the system.

In addition to calculating the time delay to the end of the T-wave the processor is also programmed to calculate a maximum stimulation length which is intended to ensure that stimulation ends at a time sufficient to ensure that one muscular contraction has terminated before the next expected R peak arrives.

Furthermore, the processor is programmed to check that the calculated or derived value of the time delay is greater than or equal to a delay time equivalent to a trigger delay plus a calculated delay. The trigger delay is the delay between initiation of a trigger signal delivered by the sensor corresponding to the detection of a first signal peak and the time this signal reaches the processor, and the calculation delay is the time required by the processor to calculate the delay. If the calculated delay time to the end of the T-wave is shorter than a delay time equal to the trigger delay plus the calculated delay then the processor is programmed to arbitrarily set the calculated time delay to an adapted value greater than or equal to the delay time equivalent to the trigger delay plus the calculated delay.

In addition the processor is programmed to check that the calculated time delay, or the adapted time delay, is less than or equal to the maximum stimulation length and to revise it if necessary so that it is less than the maximum stimulation length.

The processor is also programmed to calculate a duration of the electrical stimulation based on the input parameters and a maximum duration equal to the maximum stimulation length minus the calculated time delay or the adapted time delay and to check whether the calculated duration is less than or equal to the maximum duration. If it is not, then the duration has to be adapted so that it is less than or equal to the maximum duration.

In addition, the processor is programmed to open the measurement window at a time equal to the calculated time delay or the adapted delay if the delay has been adapted, plus the duration or adapted duration, if the duration has been adapted, plus a safety margin of, for example, 50 milliseconds. If the apparatus is triggered using signals derived from the electrocardiogram then this ensures that electrical stimulation signals cannot be misinterpreted as a next R peak.

The processor sends an output signal to the trigger system during the time the measurement window is closed and opens the measurement window at the calculated time permitting recognition of the detection of a further peak of the electrocardiogram by the sensor.

The trigger system will generally be a software element stored in the processor and conducted within the processor to the output channels, with suitable offsets being added to each channel, or each group of channels as desired.

This process is repeated for each successively measured R peak.

If a further signal peak is not detected after opening of the measurement window within an expected time calculated by the processor and based on a preceding value, or a preceding average value, then no trigger signal is transmitted and the transmission of the trigger signal and thus stimulation is inhibited until further signal peaks are detected within the expected limits.

Instead of using a value of the preceding time between signal peaks as a value for the R-R path it is also possible to use an average value formed from a plurality of past values. In this way it is possible for the processor to be programmed to include in the plurality of past values those values which lie within a range less than the preceding measured value plus a predefined positive deviation and more than a value corresponding to the preceding measured value less a predefined deviation. This means that only reasonable values are taken into account in forming the average value, thus increasing the reliability of the system.

The purpose of using such an average value is to improve the quality of stimulation and avoid wrong settings in the case of arrhythmia. It is known that the systole length remains more or less regular in the case of arrhythmia whereas the length of diastole can vary greatly leading to large heart rate fluctuations. In such a case it has proved successful to continue stimulation with an average history being used for calculating the delay and with stimulation occurring despite the fact that the current measured heart rate is outside of the heart rate deviation criteria that have been set. In such a case the heart rate would not be considered during the calculation of the sliding average but the stimulation is continued with the historical average for calculating a relatively correct delay to be used to stimulate after the end of systole. However, as stated above, diastole varies greatly with such a system.

If the sliding average is used then a definition must be given as to how many regular heart beats satisfying the criteria of heart rate deviation, i.e. lying within the positive and negative limits described above, can be used as a basis for determining whether, following arrhythmia, "good" recorded heart beats are included again into the sliding average to adapt to the newly prevailing situation. It has been found that a reasonable result can be obtained if three regular heart beats are detected following arrhythmia and can be included in the sliding average to adapt it to the newly prevailing situation.

Basically the determination of the heart rate, the distance between two R-R peaks could be formed from any past number of heart rates from N=1 or N>1 and any heart rate which fails the deviation test (lies outside of the maximum and minimum limits based on this average value) will not be considered for forming the sliding average until at least one regular heart beat or a plurality of regular heart beats (typically three heart beats) have been detected again. A regular heart beat means a heart beat which lies within the positive and negative limits set relative to the average heart rate.

From the foregoing it will be apparent that in the case of arrhythmia the diastole length can vary greatly so that it could happen that the expected end of muscle contraction is later than the time at which an unexpected next R peak appears. Since a muscle contraction has been started it cannot be influenced any more when the unexpected next R peak has been measured and this would lead to an undesirable situation in which the muscle contraction would end in the first phase of systole, in which we have a somewhat detrimental effect on hemodynamics.

The present apparatus is able to avoid such a situation by providing a first simulation train with a short duration just sufficient to create a first short muscle contraction (for example a stimulation train duration of 3 to 5% of R-R). Then, when the muscle contraction starts to deteriorate, which can be calculated proportional to the muscle contraction duration, for example an approximate value of 50% of the muscle contraction duration can be used (the muscle contraction duration being significantly longer than the electrical stimulation duration), a new shorter train of stimulation pulses is sent in the same channel which leads to an extension of the muscle contraction time. Such second, third, fourth electrical stimulation pulses will have typically the same parameters as the first one (although they could be different) but will be as short as possible; one or just a few stimulation pulses with intervening intervals will be used to create a small extension in time of the muscle contraction. These further stimulation pulses are then repeated until either the calculated end of muscle contraction is reached based on the prediction of the last or average heart rate, or until the next R peak is detected, whichever happens first.

The incremental muscle contraction time associated with each further stimulation pulse or train of pulses should be as small as physiologically possible in order to achieve a good control of the end of muscle contraction.

The ideal situation would be for the calculated muscle contraction to be terminated within a window of 85 to 95% of the R-R distance. In the case of arrhythmia being detected when the next R peak comes earlier (or much later), then the processor is preferably programmed to change to a mode of not adding any further short train for creating incremental muscle contraction as soon as the next R peak is detected.

Experiments have shown that the muscle contraction length is about three times the duration of electrical stimulation.

If stimulation is carried out with a pulse repetition frequency of 150 Hz then each pulse cycle lasts for 6.66 milliseconds. With a biphasic rectangular signal as shown in FIG. 2B the width of the biphasic pulse is typically one millisecond and thus the interval to the next biphasic pulse at the end of the first biphasic pulse is 5.66 milliseconds.

If the first electrical stimulation pulse train is selected to have a length of approximately 3% R-R then, for a heart rate of 60 per minute, this amounts to a total of 30 milliseconds of stimulation and this will include five biphasic pulses of 6.66 milliseconds duration of 150 Hz. This would result in an initial muscle contraction time of 90 milliseconds. Thereafter it is proposed that increments of one biphasic pulse would be sent every 10 milliseconds to continue the muscle contraction. Each biphasic pulse of 6.66 milliseconds will create an incremental muscle contraction of typically 20 milliseconds.

With a first muscle contraction time of 90 milliseconds the declining ramp of the muscle contraction takes about 50 milliseconds so that in the worst case the next R trigger being measured after an incremental stimulation would take another 50 milliseconds after the next R trigger before the muscle contraction comes to an end. Since the R trigger arrives at about 20 milliseconds after Q of the QRS complex and the technical delay of this trigger signal is typically another 25 milliseconds, this means that in the worst case the contraction ends 50 milliseconds or 5% after the R peak.

This discussion shows the benefit of using an additional non-electric sensor. Because the gating interval to open and close the measurement window or gate for the measurement of the next R peak is a little cumbersome and could lead to the next R peak being missed, because it happens during the period the gate is closed, it would be beneficial to use a non-electrical sensor to detect the different phases of the heart rhythm in correlation with the electrocardiogram. The R peaks can then be derived from the sensed heart rhythm (or the timing process can be carried out with reference to other signal peaks and the R peaks ignored—which is fundamentally also possible). Using such a non-electrical sensor the different phases of the electrocardiogram can be reliably detected despite electrical noise, and a reliable detection of the end of each heart cycle is possible which can be used to terminate the muscle contraction by terminating the supply of additional stimulating pulses, if these are still being supplied because the R peak has arrived earlier than expected. By non-electrical sensor is meant a sensor which does not detect voltages or currents related to the operation of the heart but, for example, relies on pressure or noise measurements to sense the heart rhythm. The term non-electrical sensor does not exclude sensors which use electrical or electronic techniques to detect pressure or noise signals. A non-electrical sensor would not detect the stimulation impulse and consequently only trigger on the following P-wave or QRS complex or pressure change, depending on whatever non-electrical sensing system is being used.

Figure 5:
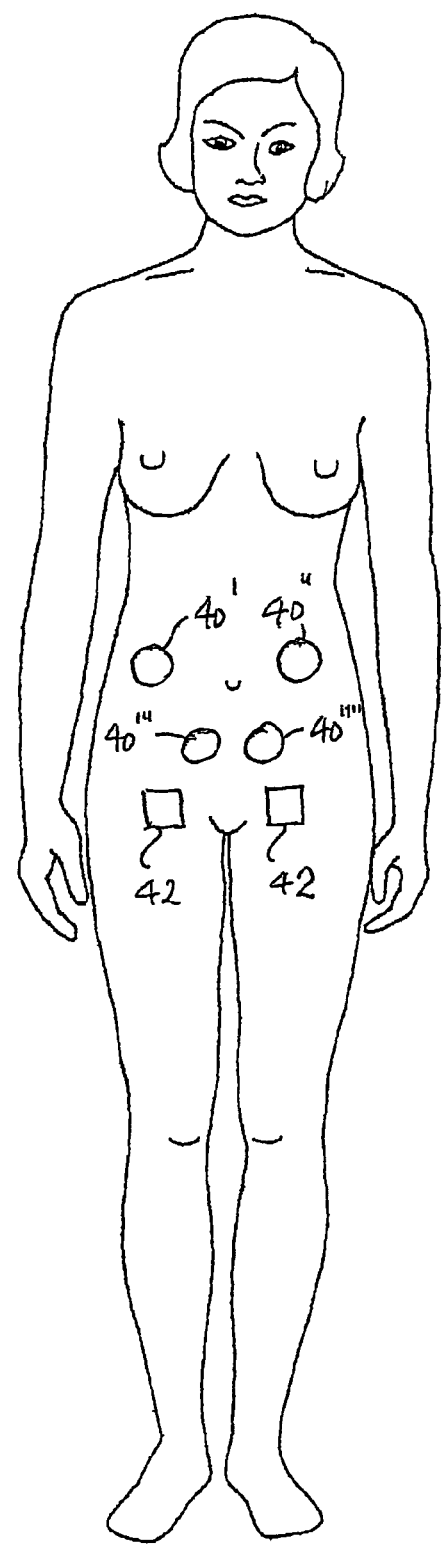
FIG. 5 is a first diagram showing one possibility for the placement of electrodes on a person.

Turning now to FIG. 5 there can be seen a schematic drawing of four active electrodes 40', 40", 40''' and 40'''' arranged generally in the abdominal region of a woman. In this case the active electrodes 40' and 40" are placed over the left and right lateralis muscles and the electrodes 40''' and 40'''' are provided over the left and right infra umbilicalis muscles. The passive electrodes 42 are placed over the infra inguinalis muscles. The placement of these electrodes is given purely by way of example and is not to be understood as any restriction on the positioning of electrodes in practice.

It is now assumed that the electrotherapy apparatus is designed to have two groups of output channels, each group comprising four distinct output channels. Thus the channels 1 to 4 belong to group A and channels 5 to 8 belong to group B. The signals on output channel 1 and on output channel 5 are connected via respective leads to the electrode 40'. The signals on channels 2 and 6 are connected via respective leads to the electrode 40''. The signals on channels 3 and 7 are connected via respective leads to electrode 40''' and the signals on channels 4 and 8 are connected via respective leads to electrodes 44'.

Figure 6:
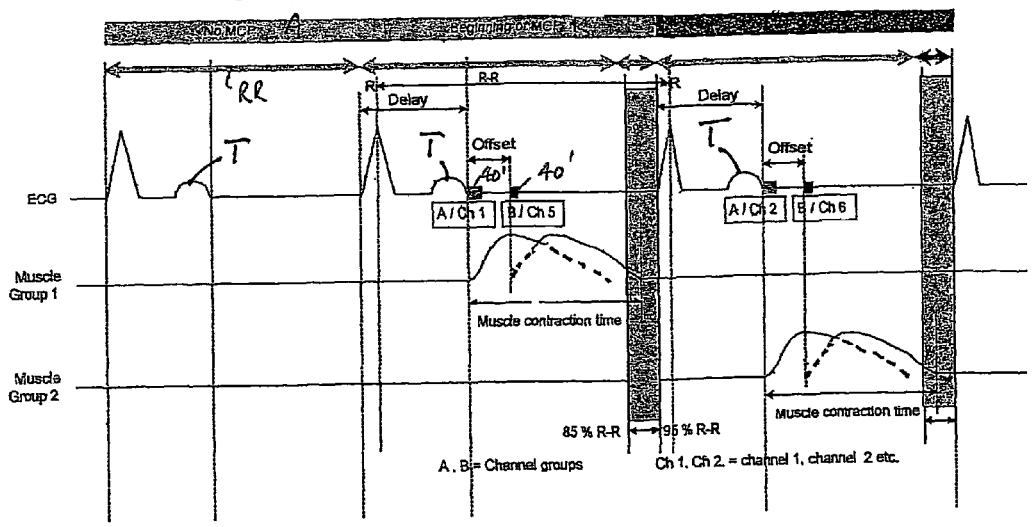
FIG. 6 is a diagram explaining how the electrodes shown in example 5 can be provided with stimulation signals from two different channel groups.

FIG. 6 now shows how this basic arrangement operates.

The top curve in FIG. 6 shows a schematic representation of an electrocardiogram and is divided into three sections A, B and C, as in FIG. 3, so that the section A illustrates the situation when no counter-pulsation electrotherapy is taking place, section B is the start of counter-pulsation electrotherapy and section C is the "steady state" process.

The electrotherapy apparatus measures the distance R-R in section A and calculates from it a delay to the end of the T-wave at which time channel 1 of group A applies a trigger pulse shown as a grey square to an electrode 40'.

Channel 4 of group B is controlled by the processor with an offset shown in section B to send a trigger pulse to the same electrode 40' at the time the respective muscle, i.e. the left-hand lateralis muscle in FIG. 5, has reached its maximum contraction. The effect of this extra stimulation pulse is to increase the duration of muscle contraction so that it now extends over the period identified in FIG. 6 as muscle contraction time to a position within the window 85% R-R to 95% R-R.

During the next heart beat (section C) no signals are applied to the electrode 40' but instead are applied to the electrode 40'' associated with muscle group 2, i.e. the right-hand lateralis muscle group. Again signals are applied to the electrode 40'' from the groups A and B and specifically from channel 2 of group A and channel 6 of group B. In the next heart beat no signals are applied to the electrodes 40' and 40'' but instead to the electrode 40'''. Then, in the next heart beat the signals are applied to the electrode 40'''' and then the situation repeats again. The signals for the electrodes 40''' and 40'''' are not shown in FIG. 6 because this would unnecessarily complicate the representation.

It will be noted that the muscle contraction for each stimulating pulse is essentially a slightly asymmetrical hump with a faster rise time (typically equivalent to the offset in sections B or C in the example of FIG. 6) and with a longer decay time (typically twice the rise time). Because the muscle contraction caused by stimulating pulse of channel 1 of channel group A is supplemented by the stimulating pulse of channel 5 of channel group B it does not actually complete the decay process but rather rises again shortly after a further time equivalent again, in this example, to the offset. For this reason both the decaying part of the first hump and the corresponding rising part of the second hump are shown in broken lines in the drawing. It is only the envelope curve in solid lines which shows the actual muscle contraction.

With two channel groups the electrodes that are used are provided with multiple pin connectors so that the pins of one electrode are connected to channels 1 and 5 of channel groups A and B, etc. If three channel groups are provided then the pins of each active electrode are connected to three channels, for example channel 1, channel 5 and channel 9 of channel groups A, B and C respectively.

This means that the train of channel group B is supplied to the same muscle group as the one from channel group A; i.e. the train from channel group A will lead to a muscle contraction of the connected electrode and, after a defined offset, a second train which is the same or different from the first one (or third train if channel B is being used) of impulses follows at a time when the muscle contraction resulting from the first train of channel group A is still prevailing. This second (or third) train will extend the muscle contraction time to end in a wanted time window relative to R-R.

Figure 7:
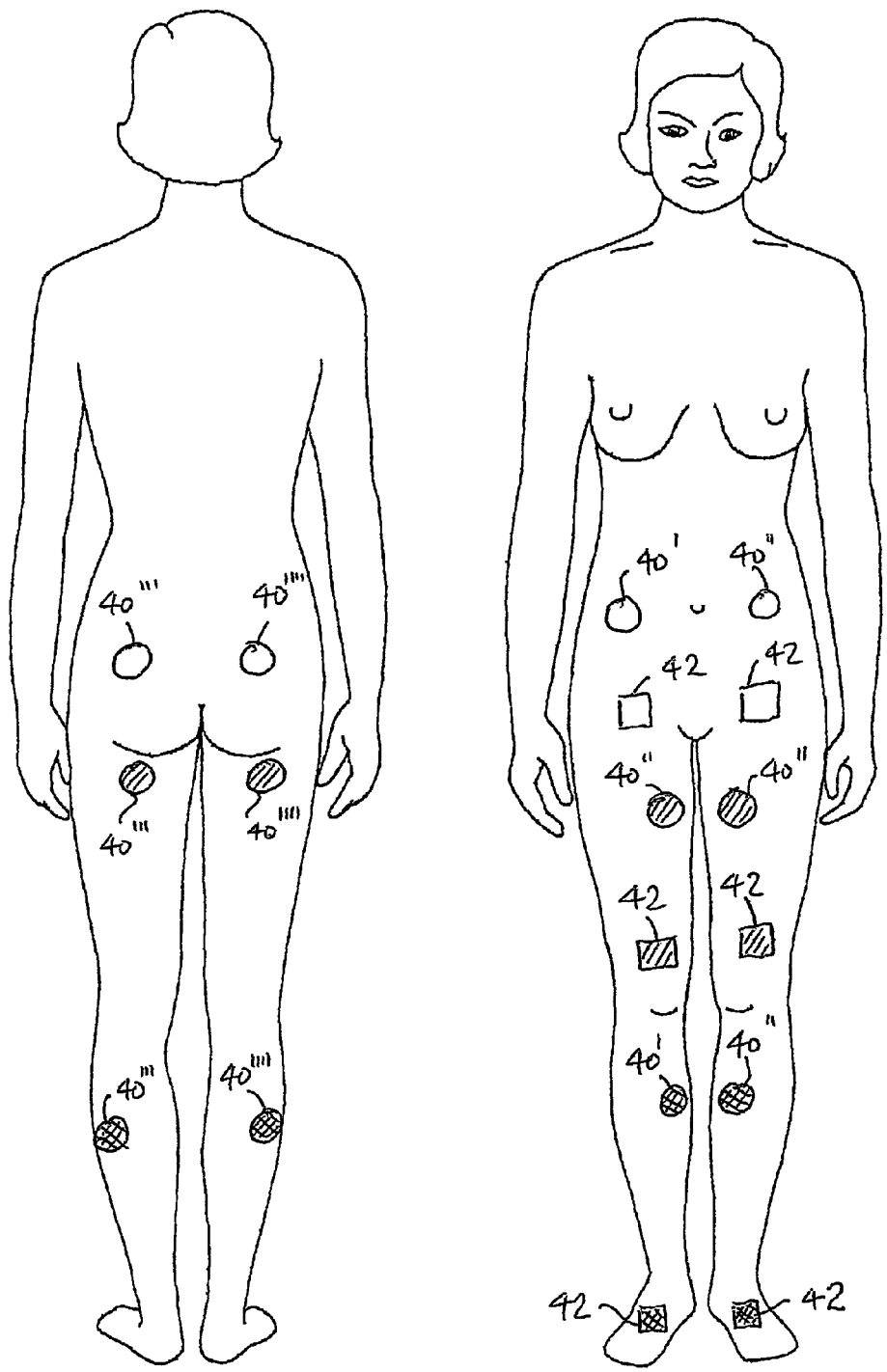
FIG. 7 is a further diagram illustrating the placement of active electrodes on a person.

Turning now to FIG. 7 there is shown a woman who has been provided with a variety of electrodes 40', 40'', 40''', 40'''' and corresponding passive electrodes 42. The electrodes shown as circles with a white interior are associated with a group A of four channels. The circular electrodes with single hatching are associated with a group B of four channels and the four electrodes with cross-hatching are associated with a group C of four channels. The passive electrodes 42 associated with each group of channels are shown as squares. They are electrically equivalent and are unhatched for channel group A, single-hatched for channel group B and cross-hatched for channel group C.

The electrodes 40' and 40'' of group A are provided over the left and right lateralis groups of muscles. The electrodes 40''' and 40'''' of the group A are provided over the left and right glutea muscles. The passive electrodes 42 associated with group A are placed over the infra inguinalis muscles.

The electrodes 40' and 40'' of group B are provided over the left and right femoralis medialis muscles whereas the electrodes 40''' and 40'''' associated with group B are provided over the left and right sulcus glutealis muscles. The passive electrodes associated with channel group B are provided over the left and right supragenus muscles.

The electrodes 40' and 40'' associated with channel group C are provided over the left and right medialio muscles whereas the electrodes 40''' and 40'''' are provided over the left and right lateralis muscles of the calf. The passive electrodes 42 associated with channel group C are provided over the doralis pedis muscles on the left and right feet of the woman.

Thus, in this embodiment the circular non-hatched electrodes 40' to 40'''' and the associated passive electrodes 42 are associated with the regio adominis/glutea muscles. The single-hatched electrodes 40' to 40''' and the associated single-hatched passive electrodes 42 are associated with the region glutea-femoralis muscles.

The double-hatched electrodes 40' to 40'''' and the cross-hatched passive electrodes 42 are associated with the region cruralis muscles.

There are several main ways of operating the electrotherapy apparatus with a patient provided with the electrodes as shown.

Figure 8:
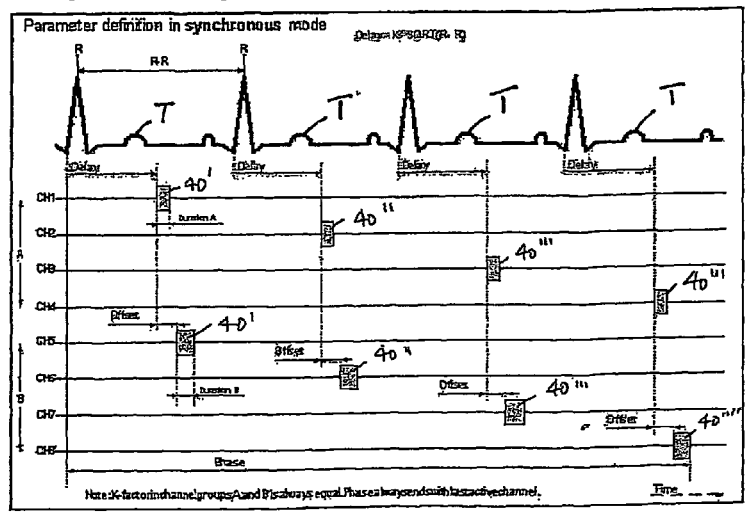
FIG. 8 is a diagram to explain how the electrodes of FIG. 7 can be supplied with stimulation signals.

Before explaining how the electrotherapy apparatus of the invention is used in connection with FIG. 7 it is now helpful to consider FIG. 8. This shows how, for the channel group A comprising channels 1 to 4, which are associated with the non-hatched electrodes 40' to 40'''' of FIG. 7, the stimulating pulses are applied from channel 1 to electrode 40', from channel 2 to electrode 40'', from channel 3 to electrode 40''' and from channel 4 to electrode 40'''', in each case at a time just after the end of the T-wave.

Moreover it shows how, for the channel group B, comprising the channels 5, 6, 7 and 8, the stimulating signals transmitted by those channels are later than the stimulating signals transmitted by the corresponding channels of channel group B by an amount labelled offset. These signals are applied in the scheme of FIG. 6 to the single-hatched electrodes 40' to 40''''. Not shown in FIG. 8 is the channel group C comprising channels 9 to 12 which is associated with the cross-hatched electrodes 40' to 40'''' and where the electrical stimulating signals are provided with an offset which is twice the value of the offset of the signals of channel B (the value twice is chosen arbitrarily and although preferred in this case is not to be understood to be restrictive).

When the electrotherapy apparatus is operated in this mode then the effect will be to increase the pumping of blood from the heart to the periphery. This will lead to improved peripheral arterial perfusion and expediently also to an increase of venous return.

Another possibility exists of exploiting the electrodes in the arrangement shown in FIG. 7. In this case the electrodes are connected differently to the electrotherapy apparatus. More specifically, the non-hatched electrodes 40' to 40'''' are connected to channels 9 to 12 of channel group C. The single-hatched electrodes 40' to 40'''' are connected to channels 5 to 8 of channel group B and the cross-hatched electrodes 40' to 40'''' are connected to the channels 1 to 4 of channel group A. In each case only one channel is connected to any one electrode (as in the previous example).

With the electrodes connected in this way, and operated with the same offsets as shown in FIG. 8, i.e. with the stimulation signals being applied to the channels of channel group A at the end of the T-wave (or shortly thereafter), with the stimulation signals of channel group B being applied to respective electrodes at a later time with a suitable offset value, and with the stimulation signals of channel group C being applied to the associated electrodes with a larger offset time, then the effect is to direct blood flow from the periphery back to the heart.

A similar effect can be achieved with only two channel groups A and B, by placing the electrodes of the channel group A either in the region cruralis or region glutea-femoralis and the electrodes of channel group B in the area of the region glutea-femoralis or region abdominis/glutea. Essential is that the electrodes of the different groups are close in body areas which have a significant difference in their distance from the heart. To direct the effect from the periphery to the heart, the electrodes of the channel group stimulating later (due to the offset) are placed closer to the heart than the ones from the channel group stimulating earlier.

At super threshold stimulation, i.e. with amplitudes close to the maximum which are accepted as painless by the volunteer or patient (for example 20 to 45 V depending on the location of the electrodes), an increase of the pressure pulse wave (an increase in the hump in FIG. 3 during early diastole) will lead to increased coronary perfusion. An increase of arterial retrograde displacement back to the heart, an increase of venous return and an increase of lymph drainage from the periphery to the heart will also occur. This will improve central hemodynamics (increase the hump in FIG. 3) and increase the cardiac output. This setting is recommended for patients having too low cardiac output or after cardiac shock.

At a threshold level of stimulation, i.e. at a level of muscle contraction which is just about perceivable by the observing medical practitioner or by the patient (typically around 10 V), there will be an increase of retrograde pressure wave propagation back to the heart (increasing the heart in early diastole as described with reference to FIG. 3) and that will improve central hemodynamics. It is noted that this effect cannot be achieved by any other known counter-pulsation methods because these only operate at maximum amplitudes, because they need such high amplitudes to achieve an improvement in central hemodynamics.

The following definitions have been used in this application.

A channel is an output of the electrotherapy apparatus which delivers a stimulation signal to an active skin electrode leading to one muscle group contracting, when used in connection with one passive (neutral) electrode placed in its vicinity.

A channel group consists of a specific number X of channels (the typical example being four channels), in which the stimulation signal is distributed in a sequencing mode thereby resulting in one specific muscle group being contracted for each heart beat so that a number of muscle groups corresponding to the number of channels can be contracted one after the other thus giving each particular muscle a rest of X minus 1 heart beats. For example, with X=4 channels the rest is three heart beats. This is a key feature to avoid muscle fatigue. More than four channels (or less) can be designed into a channel group if required.

The number of channels in a channel group is fixed for a particular piece of electrotherapy apparatus because the printed circuit leading to the channel outlets must be laid out accordingly.

The number of active channels can be determined by the programming of the firmware (software for the microprocessor) to be less than or equal to the maximum number of channels. Thus, it permits the number of channels X for which sequencing takes place to be reduced. As an example if there are four active channels then the sequencing is being done with all channels of the channel group, i.e. channel 1, channel 2, channel 3, channel 4, channel 1, channel 2, etc. Active channel=2 would mean sequencing is being done with only two channels, i.e. channel 1, channel 2, channel 1, channel 2, channel 1, etc., channels 3 and 4 being inactive.

Multiple channel groups: A device can be equipped with more than one channel group. If two channel groups are provided with four channels each then the total number of channels is eight.

The number of channel groups Y is fixed for a particular electrotherapy apparatus because the printed circuit board leading to the channel outlets must be laid out accordingly.

With multiple channel groups sequencing can be done in parallel; i.e. for example with two channel groups, channel 1, channel 5 operate simultaneously, channel 2 and channel 6 operate simultaneously, channel 3 and channel 7 operate simultaneously and channel 4 and channel 8 operate simultaneously, using the same delay for both channel groups. Alternatively different delays can be used for each of the channel groups.

All variable stimulation parameters, for example the delay, the amplitude, the frequency and duration of the stimulation pulse trains as well as the amplitude and the frequency variation as a function of time within a train of stimulation pulses or multiple trains of the same or different configuration, can principally be set individually for each channel group.

The same is the case for the selection of active channels in each channel group, which can in principle be selected differently. It is however more comfortable for the person being treated, and advisable for enhancing heart unloading effect, to always use the same muscles that are being stimulated synchronously in the selected sequencing mode, meaning that the active channels are being selected automatically to be the same in all active channel groups. For example, with X=4× 2=8 channels this means that with only two active channels being selected for channel groups A and B the sequencing will be done in the following sequence: channel 1 plus channel 5, channel 2 plus channel 6, channel 1 plus channel 5, etc. The firmware is programmed in such a way that although a number Y of channel groups has been built into the electrotherapy apparatus any number less than or equal to Y can be activated by selection. If only one channel group is selected then only the channels of this group are active. This means that with this example, with X=4 one can select 4, 3, 2 or 1 active channels and if one selected Y=2 then one can have 8, 6, 4 or 2 channels or, with Y=1, one can have 4, 3, 2, 1 channels being active, depending on the selection made.

Offset means, as explained above, that a time difference is defined (plus or minus) by which the channels of one group stimulates earlier or later than the channels of another group. This timing difference can be achieved by deducting or adding the offset value to the set delay in the respective channel group.

If Y is selected to be greater or equal to 2 then another offset is possible between channel group C and B; i.e. more than one offset can be provided in the same electrotherapy apparatus.

Thus the purpose of multiple channel groups is for example to increase the active muscle mass to increase displaced blood flow or lymph drainage and herewith achieve an increase in overall metabolism in angiology.

The use of multiple channel groups also makes it possible to increase muscular work and increase the displaced blood flow or lymph drainage and in this way to increase overall metabolism. The use of offset permits contractions in a sequence given by the time difference of the offset and with this to give the effects achieved a direction, either a) from the periphery to the heart or b) from the heart to the periphery.

Figure 9:
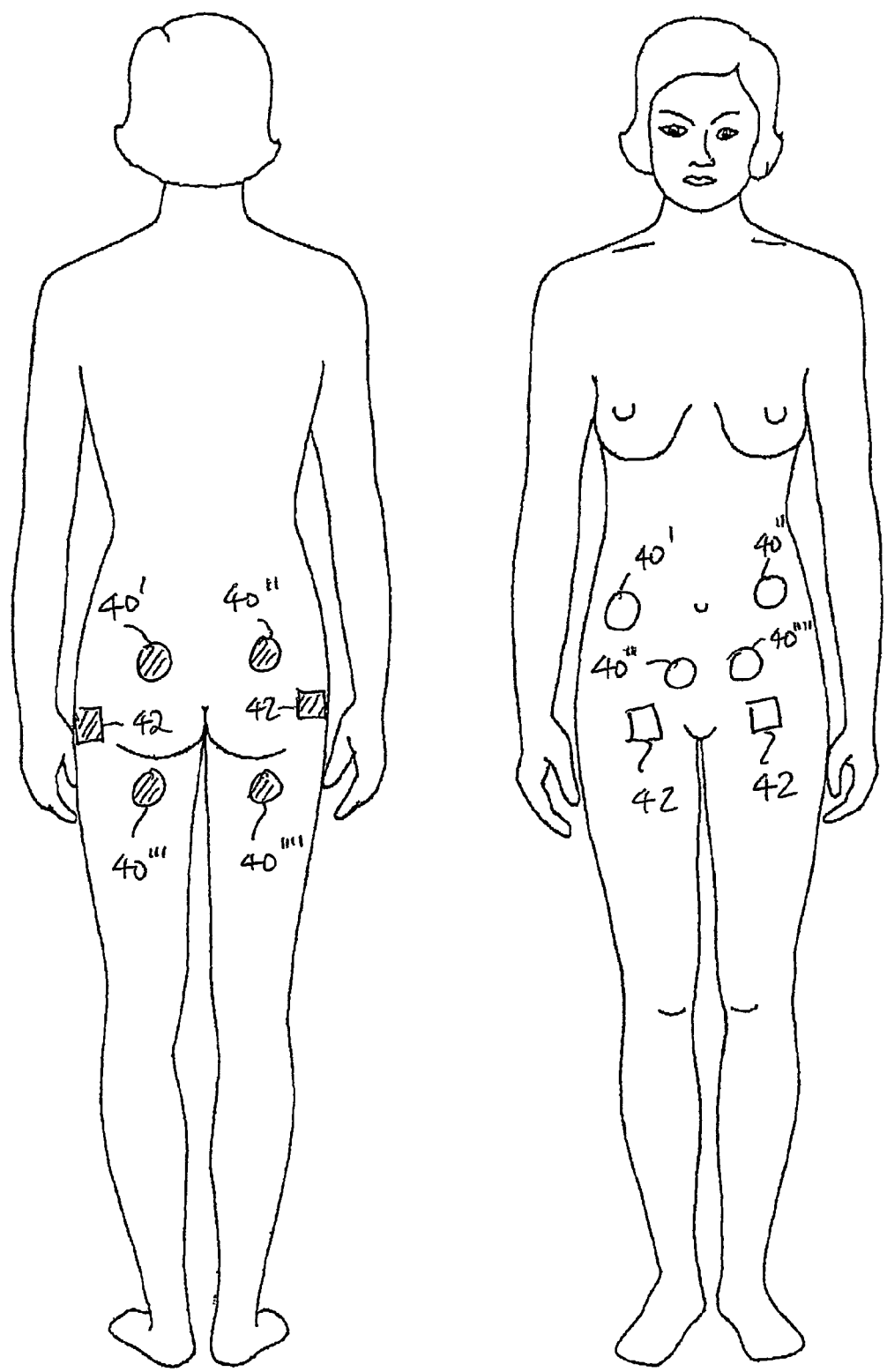
FIG. 9 is another diagram showing a possible placement of electrodes on a person.

Another possible arrangement of electrodes is shown in FIG. 9. The same convention has been used in this example for the designation of the electrodes as in the example of FIG. 7. That is to say, the non-hatched electrodes 40' to 40"" are associated with a channel group A and the single-hatched electrodes 40' to 40"" are associated with the channel group B. In this arrangement the non-hatched electrodes 40' to 40"" are placed so that the electrodes 40' and 40" will lie over the left and right lateralis muscles while the non-hatched electrodes 40'" and 40"" lie over the left and right infra umbilicalis muscles. The associated non-hatched passive electrodes 42 lie over the left and right infra inguinalis muscles.

The single-hatched electrodes 40' and 40" lie over the left and right glutea muscles whereas the single-hatched electrodes 40'" and 40"" lie over the sulcus gluteallis muscles. The single-hatched passive electrodes 42 associated with channel group B are placed here over the infra gluteallis muscles.

The purpose of this arrangement is to soften the perceived impact on effects of increased muscle mass at the same distance from the heart resulting in increase of arterial retrograde flow and arterial blood displacement. The results are pronounced in the regio abdominus.

At super threshold stimulation and with an offset=0 (i.e. no offset between stimulation signals between channel group A and channel group B) the amplifying effects are highest with the biggest influence on the aorta and veina carva resulting in improved central hemodynamical heart unloading via pulse wave propagation (increase of hump in early diastole with an increase of coronary perfusion). However such stimulation can be perceived as too strong. Using an offset between the channels of channel group A and channel group B results in the softening of the perceived impact and allows benefit to be achieved from improved results.

In the arrangement of FIG. 5 with multiple channel groups it is possible to use these to extend the muscular contraction time in the stimulated muscle groups in order to improve hemodynamics.

Ideally muscle contractions will terminate before the next R peak, in a time window of 85% to 100% of R-R within the R-R heart cycle within which the respective muscle contraction has been started and a situation should be avoided in which the muscle contraction ends in the following systole phase, i.e. after the following R peak.

Controlling the end of muscle contraction together with the control of the beginning of muscle contraction to coincide within the defined window of −5% of R-R before the end of systole (end of T-wave) and a +45% of R-R after the end of systole (end of T-wave) results in a general improvement of overall hemodynamic results of heart unloading, typically 20%, when compared to controlling the beginning of the muscle contraction only.

It should also be noted that the aforementioned examples have all been described with reference to synchronous electro-stimulation, i.e. to electro-stimulation when the pulses supplied are synchronized with the actual patient's heart rate.

It is however also possible to use the electrotherapy apparatus of the present invention in an asynchronous mode. Asynchronous stimulation means a stimulation mode which is particularly beneficial for wellness. In accordance with the present invention this can be implemented in an auto-program mode in which the electrotherapy apparatus starts with a synchronous phase and should end with an asynchronous phase, with one asynchronous phase or alternating asynchronous and synchronous phases between the starting and end phases. The asynchronous mode of stimulation is to be understood here as a form of stimulation whereby the heart rhythm is not used for synchronization but instead stimulation is being repeated with a fixed variable cycle time, however using the same sequencing modes as for the synchronous mode for stimulation.

One purpose of this is as follows: During the asynchronous phase the muscular work that is effected is increased and this intensifies lipolysis. During asynchronous stimulation, heart unloading is reduced or might even change to heart loading but with the following synchronous phase heart unloading will follow. With this procedure the overall heart unloading of such a combined auto-program mode is less than with a pure synchronous mode. However heart unloading is still much better than with a purely asynchronous mode as used in many conventional muscle stimulators.

The apparatus or circuit used to generate or trigger the electrical stimulation pulses can be the apparatus described in the simultaneously filed European patent application entitled "Electrotherapy Apparatus", the content of which is incorporated into the present application by reference. In addition the content of the simultaneously filed European patent application entitled "Electrotherapy Apparatus And Method Of Treating A Person Or A Mammal Using Such Electrotherapy Apparatus" is also incorporated herein by reference.

The invention claimed is:

1. An electrotherapy apparatus comprising a sensor for detecting periodically recurring signal peaks, a signal processor for deriving from said periodically recurring signal peaks a time delay corresponding to approximately the end of a T-wave, a trigger system or a circuit initiated by an output signal of said signal processor or embodied within said signal processor for applying electrical stimulations to one or more active electrodes provided on the said person at a derived time delay related to the end of said time delay, in synchronization with the heart rhythm in the counterpulsation mode, the signal processor being adapted:

a) to make a determination for successive pairs of signal peaks of a value corresponding to the time between said successive pairs of signal peaks and thus to the said person's heart rate, b) to compare said value with maximum and minimum permissible technical limits permitted by the apparatus and/or
c) to compare said value with maximum and minimum permissible selected limits,
d) to determine whether each said value derived in step a) exceeds a preceding value or a preceding value averaged over a plurality of heart beats by more than a defined amount,
e) to determine whether each said value derived in step a) is less than a preceding value or a preceding value averaged over a plurality of heart beats by more than a defined amount,
f) to trigger said trigger system or circuit only when the comparisons b) and/or c) are favourable and the determinations d) and e) show that the said value derived in step a) does not exceed the preceding value or the preceding average value by more than the defined amount and is not less than the preceding value or the preceding value by more than the defined amount,
g) to close a measurement window for said sensor once a determination is made that the comparisons b) and/or c) are favourable and that the determinations d) and e) show that the said value derived in step a) does not exceed the preceding value or the preceding average value by more than the defined amount and is not less than the preceding value or the preceding average value by more than the defined amount, said measurement window being closed prior to triggering said trigger system,
h) to calculate in addition to said time delay a maximum stimulation length,
i) to check that the derived value of said time delay is greater than or equal to a delay time equivalent to a trigger delay plus a calculation delay, said trigger delay being the delay between initiation of a trigger signal delivered by said sensor corresponding to the detection of a first signal peak and the time this signal reaches the processor and the calculation delay being the time required by the processor to derive the delay,
j) to check that the derived time delay is less than or equal to said maximum stimulation length and to revise said derived time delay if necessary so that it fulfils the two conditions derived time delay greater than or equal to the trigger delay plus the calculation delay and derived time delay less than or equal to the maximum stimulation length,
k) to calculate a maximum duration equal to the maximum stimulation length minus the time delay,
l) to calculate a duration of said electrical stimulation and a maximum duration value equal to said maximum stimulation length minus said derived time delay and to check whether said calculated duration is less than or equal to said maximum duration and if not to adapt it so that it is less than or equal to said maximum duration,
m) to calculate an open measurement window time equal to said derived time delay, or said adapted delay, if said delay has been adapted, plus said duration or said adapted duration, if said duration has been adapted, plus a safety margin, and
n) to send an output signal to said trigger system during said measurement window and open said measurement window at the calculated time permitting the recognition of the detection of a further peak of said electrocardiogram by said sensor.

2. An electrotherapy apparatus in accordance with claim 1, wherein said signal processor is adapted to repeat the sequence of steps based on the new R-R value.

3. An electrotherapy apparatus in accordance with claim 2, wherein, if a further signal peak is not detected after opening of said measurement window within an expected time calculated by said signal processor based on a preceding value or a preceding average value, no trigger signal is transmitted and transmission of a trigger signal and thus stimulation is inhibited until further signal peaks are detected within expected limits.

4. An electrotherapy apparatus in accordance with claim 1, wherein, instead of using a value of the preceding time between signal peaks as said value, an average is formed from a plurality of past values.

5. An electrotherapy apparatus in accordance with claim 4, wherein the signal processor is adapted to include in said plurality of past values only those values which lie within a range less than the preceding measured value plus a predefined positive deviation and more than a value corresponding to the preceding measured value less a predefined deviation.

6. An electrotherapy apparatus in accordance with claim 1, wherein the apparatus has a plurality of channels for applying electrical stimulations to one or more active electrodes provided on the said person and in that for each said channel a respective offset value is added to said delay.

7. An electrotherapy apparatus in accordance with claim 4, wherein the apparatus has a plurality of channels for applying electrical stimulations to one or more active electrodes provided on the said person and in that for each said channel a respective offset value is added to said delay.

8. An electrotherapy apparatus in accordance with claim 1 wherein the signal peaks are R-R peaks of an electrocardiogram of a person.

9. An electrotherapy apparatus comprising a sensor for detecting periodically recurring signal peaks, a signal processor for deriving from said periodically recurring signal peaks a time delay corresponding to approximately the end of a T-wave, a trigger system or a circuit initiated by an output signal of said signal processor or embodied within said signal processor for applying electrical stimulations to one or more active electrodes provided on the said person at a derived time delay related to the end of said time delay, in synchronization with the heart rhythm in the counterpulsation mode, the signal processor being adapted:
a) to make a determination for successive pairs of signal peaks of a value corresponding to the time between said successive pairs of signal peaks and thus to the said person's heart rate,
b) to compare said value with maximum and minimum permissible technical limits permitted by the apparatus and/or
c) to compare said value with maximum and minimum permissible selected limits,
d) to determine whether each said value derived in step a) exceeds a preceding value or a preceding value averaged over a plurality of heart beats by more than a defined amount,
e) to determine whether each said value derived in step a) is less than a preceding value or a preceding value averaged over a plurality of heart beats by more than a defined amount,
f) to trigger said trigger system or circuit only when the comparisons b) and/or c) are favourable and the determinations d) and e) show that the said value derived in step a) does not exceed the preceding value or the preceding average value by more than the defined amount and is not less than the preceding value or the preceding value by more than the defined amount, g) to suppress said trigger if a state of arrhythmia is detected from the successive pairs of signal peaks, h) to close a measurement window for said sensor once a determination is made that the comparisons b) and/or c) are favourable and that the determinations d) and e) show that the said value derived in step a) does not exceed the preceding value or the preceding average value by more than the defined amount and is not less than the preceding value or the preceding average value by more than the defined amount, said measurement window being closed prior to triggering said trigger system, i) to calculate in addition to said time delay a maximum stimulation length, j) to check that the derived value of said time delay is greater than or equal to a delay time equivalent to a trigger delay plus a calculation delay, said trigger delay being the delay between initiation of a trigger signal delivered by said sensor corresponding to the detection of a first signal peak and the time this signal reaches the signal processor and the calculation delay being the time required by the signal processor to derive the delay, k) to check that the derived time delay is less than or equal to said maximum stimulation length and to revise said derived time delay if necessary so that it fulfils the two conditions derived time delay greater than or equal to the trigger delay plus the calculation delay and derived time delay less than or equal to the maximum stimulation length, l) to calculate a maximum duration equal to the maximum stimulation length minus the time delay, m) to calculate a duration of said electrical stimulation and a maximum duration value equal to said maximum stimulation length minus said derived time delay and to check whether said calculated duration is less than or equal to said maximum duration and if not to adapt it so that it is less than or equal to said maximum duration, n) to calculate an open measurement window time equal to said derived time delay, or said adapted delay, if said delay has been adapted, plus said duration or said adapted duration, if said duration has been adapted, plus a safety margin, and o) to send an output signal to said trigger system during said measurement window and open said measurement window at the calculated time permitting the recognition of the detection of a further peak of said electrocardiogram by said sensor.

\* \* \* \* \*